(12) United States Patent
Paul

(10) Patent No.: US 12,317,907 B2
(45) Date of Patent: Jun. 3, 2025

(54) HYDROLYSATE OF WATER SOLUBLE INSECT PROTEINS AND METHOD FOR PREPARATION THEREOF

(71) Applicant: Protix B.V., Dongen (NL)

(72) Inventor: Aman Paul, Rijen (NL)

(73) Assignee: Protix B.V., Dongen (NL)

( * ) Notice: Subject to any disclaimer, the term of this patent is extended or adjusted under 35 U.S.C. 154(b) by 265 days.

(21) Appl. No.: 17/641,821

(22) PCT Filed: Sep. 16, 2020

(86) PCT No.: PCT/NL2020/050572
§ 371 (c)(1),
(2) Date: Mar. 10, 2022

(87) PCT Pub. No.: WO2021/054824
PCT Pub. Date: Mar. 25, 2021

(65) Prior Publication Data
US 2024/0041068 A1 Feb. 8, 2024

(30) Foreign Application Priority Data

| Sep. 17, 2019 | (NL) | 2023838 |
| Dec. 17, 2019 | (NL) | 2024481 |
| May 11, 2020 | (NL) | 2025546 |
| May 11, 2020 | (NL) | 2025547 |

(51) Int. Cl.
| A61K 35/64 | (2015.01) |
| A23J 1/02 | (2006.01) |
| A23J 3/04 | (2006.01) |
| A23J 3/22 | (2006.01) |
| A23J 3/34 | (2006.01) |
| A23K 10/14 | (2016.01) |
| A23K 10/20 | (2016.01) |
| A23K 20/147 | (2016.01) |
| A23K 30/20 | (2016.01) |
| A23K 50/40 | (2016.01) |
| A23K 50/80 | (2016.01) |
| A23L 27/21 | (2016.01) |
| A61K 9/00 | (2006.01) |

(52) U.S. Cl.
CPC ............. *A23K 10/20* (2016.05); *A23J 1/02* (2013.01); *A23J 3/04* (2013.01); *A23J 3/227* (2013.01); *A23J 3/341* (2013.01); *A23K 10/14* (2016.05); *A23K 20/147* (2016.05); *A23K 30/20* (2016.05); *A23K 50/40* (2016.05); *A23K 50/80* (2016.05); *A23L 27/215* (2016.08); *A61K 9/0056* (2013.01); *A61K 35/64* (2013.01)

(58) Field of Classification Search
None
See application file for complete search history.

(56) References Cited

FOREIGN PATENT DOCUMENTS

| CN | 1415757 A | 5/2003 |
| EP | 2953487 A0 | 12/2015 |
| JP | 2009254348 A | 11/2009 |
| WO | 2013/191548 A1 | 12/2013 |
| WO | 2014123420 A1 | 8/2014 |
| WO | 2015134033 A1 | 9/2015 |
| WO | 2021/054824 A1 | 3/2021 |

OTHER PUBLICATIONS

Merz et al: "Flavourzyme, an Enzyme Preparation with Industrial Relevance: Automated Nine-Step Purification and Partial Characterization of Eight Enzymes", Journal of Agricultural and Food Chemistry vol. 63, No. 23, Jun. 17, 2015, pp. 5682-5693.
Firmansyah et al: "Production of protein hydrolysate containing antioxidant activity from Hermetia illucens", HELIYON, vol. 5, No. 6, Jun. 1, 2019, p. e02005.
Dong et al: Palatability of Water-Soluble Extracts of Protein Sources and Replacement of Fishmeal by a Selected Mixture of Protein Sources for Juvenile Turbot (*Scophthalmus maximus*), Ocean University of China, Science Press and Spring-Verlag Berlin Heidelberg, 2016.
Kato et al: "Role of Free Amino Acids and Peptides in Food Taste", American Chemical Society, Chapter 13, 1989.
Senevirathne et al: "Utilization of Seafood Processing By-products: Medicinal Applications", Advances in Food and Nutrition Research, vol. 65, Chapter 32, 2012.

(Continued)

*Primary Examiner* — Russell G Fiebig
(74) *Attorney, Agent, or Firm* — N.V. Nederlandsch Octrooibureau

(57) ABSTRACT

The present invention relates to a method for producing enzymatically hydrolysed water-soluble insect proteins, in particular from black soldier fly larvae protein as the protein source. In addition, the present invention relates to enzymatically hydrolysed water-soluble insect proteins and to Maillard reaction products of enzymatically hydrolysed water-soluble insect proteins, in particular from black soldier fly larvae protein as the protein source. Furthermore, the present invention relates to the use of the enzymatically hydrolysed water-soluble insect proteins or to the use of the Maillard reaction products of enzymatically hydrolysed water-soluble insect proteins. Finally, the present invention relates to a pet food product, a pet food ingredient, an animal feed product or an animal feed ingredient comprising, or consisting of, the enzymatically hydrolysed water-soluble insect proteins or the Maillard reaction products of enzymatically hydrolysed water-soluble insect proteins, and relates to a human food product or a human food ingredient comprising, or consisting of, the enzymatically hydrolysed water-soluble insect proteins or the Maillard reaction products of enzymatically hydrolysed water-soluble insect proteins.

12 Claims, 10 Drawing Sheets

(56) References Cited

OTHER PUBLICATIONS

Figure 1:
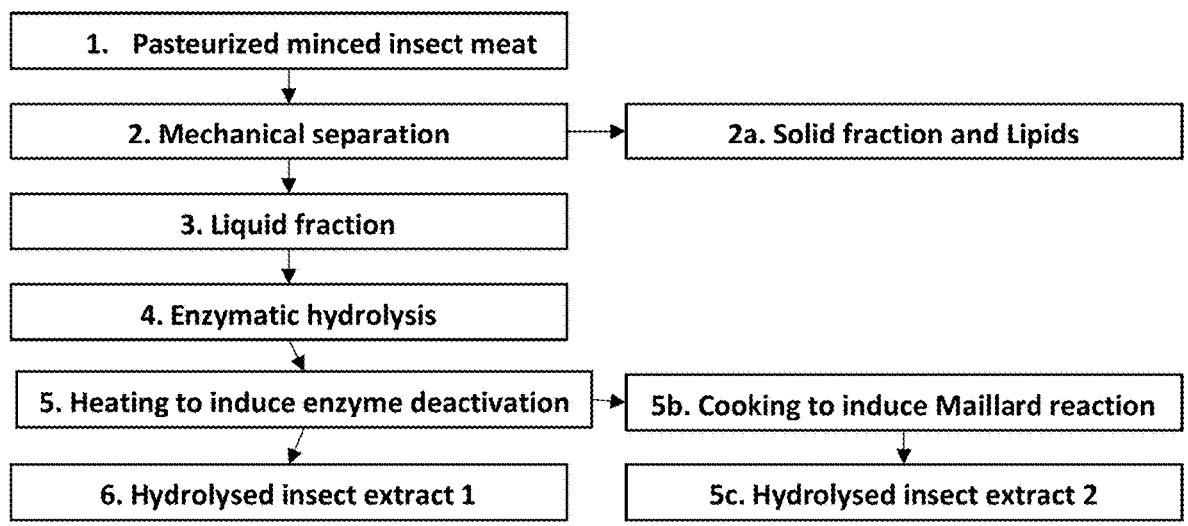

Hou et al: "Protein hydrolysates in animal nutrition: Industrial production, bioactive peptides, and functional significance", Journal of Animal Science and Biotechnology, 2017.
Anuar et al: "A review : Conversion of chicken viscera into protein hydrolysate for palatant production", Malaysian Journal of Fundamental and Applied Sciences vol. 13, No. 3, 2017, p. 606-611.
Clark: "Taste and flavour: their importance in food choice and acceptance", Proceedings of the Nutrition Society, 1998, 57, pp. 639-643.
Paul et al: "Grasshoppers as a food source? A review", Biotechnol. Agron. Soc. Environ. 2016 20(S1), p. 337-352.
Tantikitti: "Feed palatability and the alternative protein sources in shrimp feed", Songklanakarin Journal of Science and Technology, 36 (1), 51-55, Jan.-Feb. 2014.
Tchorbanov et al: "Debittering of Protein Hydrolysates by Lactobacillus LBL-4 Aminopeptidase", SAGE—Hindawi Access to Research, Enzyme Research, vol. 2011, Article ID 538676, 7 pages.
Wisuthiphaet et al: "Fish Protein Hydrolysate Production by Acid and Enzymatic Hydrolysis", KMUTUB Int J Appl Sci Technol, vol. 9, No. 4, p. 261-270, 2016.
Smetana et al: "Sustainable use of Hermetia illucens insect biomass for feed and food: Attributional and consequential life cycle assessment", Resources, Conservation & Recycling, vol. 144, 2019, p. 285-296.
Firmansyah et al: "Production of protein hydrolysate containing antioxidant activity from Hermetia illucens", Heliyon, vol. 5, 2019, p. e02005.

FIG. 2

| Parameter | Target Limit | Critical Limit | Method |
|---|---|---|---|
| Total aerobic count | <10 000 cfu/g | <100 000 cfu/g | equivalent to ISO 4833 |
| Reference: Microbiological criteria of food stuffs Regulation (EC) 2073/2005 (updated by Regulation (EC) 1441/2007): minced meat | | | |
| Enterobacteriaceae | < 10 cfu/g | < 100 cfu/g | equiv. NEN-ISO 21528-2 |
| Reference: Microbiological criteria of food stuffs Regulation (EC) 2073/2005- *egg products* | | | |
| E. Coli | < 10 cfu/g | < 100 cfu/g | Rapid'E.coli |
| Reference: Microbiological criteria of food stuffs Regulation (EC) 2073/2005- meat preparations | | | |
| Salmonella | Absent in 25g | Absent in 25g | equivalent to ISO 6579 |
| Reference: Microbiological criteria of food stuffs Regulation (EC) 2073/2005- Cooked crustacean and molluscan shellfish | | | |
| Listeria Monocytogenes | Absent in 25g | < 100 cfu/g | equiv. NEN-EN-ISO 11290-1 |
| Reference: Dutch Warenwet and Hygiene code for butchers | | | |
| Coagulase- positive staphylococcus | < 10 cfu/g | < 100 cfu/g | equiv. NEN-EN-ISO 6888-2, 37°C |
| Reference: Dutch Warenwet and Hygiene code for butchers | | | |
| Bacillus cereus | < 10 cfu/g | < 100 cfu/g | equivalent to ISO 7932 |
| Reference: Dutch Warenwet and Hygiene code for butchers | | | |
| *Clostridium perfringens* | <100 cfu/g | < 1000 cfu/g | equivalent to ISO 7937 |
| Reference: Dutch Warenwet and Hygiene code for butchers | | | |
| Campylobacter | Absent in 25g | Absent in 25g | NEN-EN-ISO 10272-1) |
| Reference: Dutch Warenwet and Hygiene code for butchers | | | |
| Yeast and moulds | <100 cfu/g | <1000 cfu/g | equivalent to ISO 21527-1/2:2008 |
| Reference: 'OECD issue paper on microbial contaminants limits for microbial pest control products' by European commission | | | |

FIG. 9
A
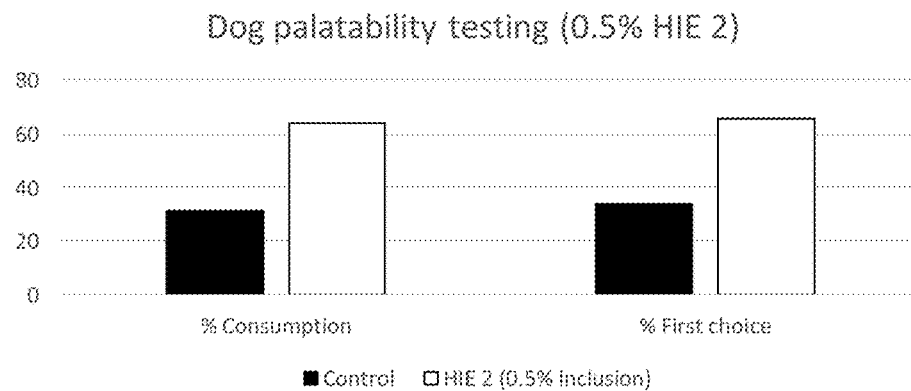
B
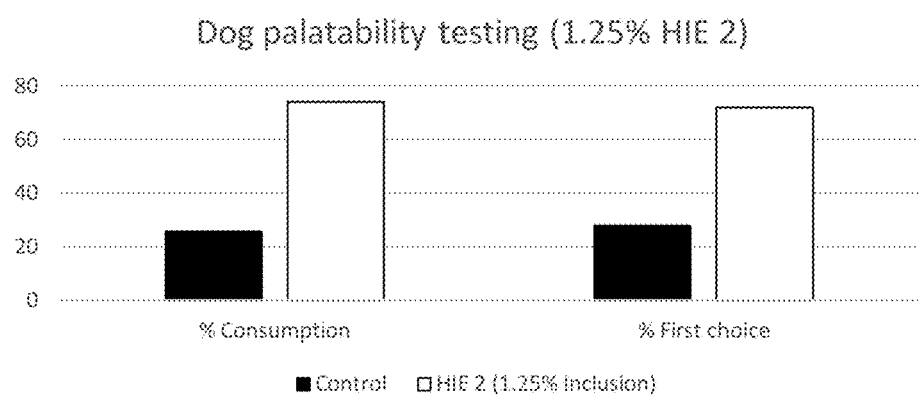
C
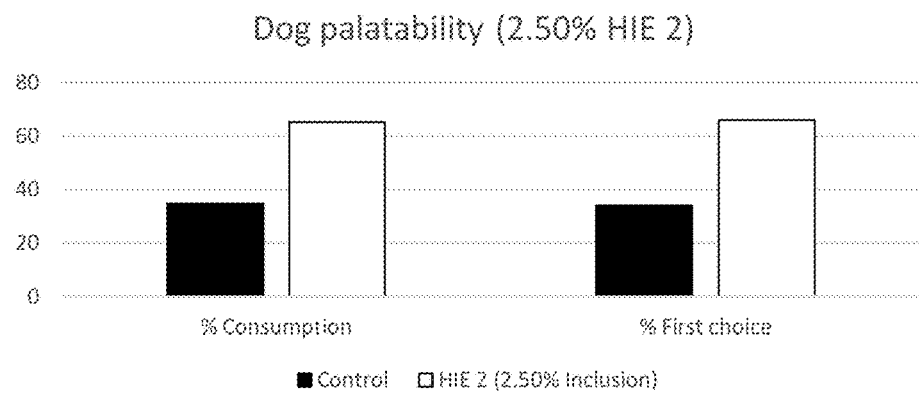

FIG. 10
A
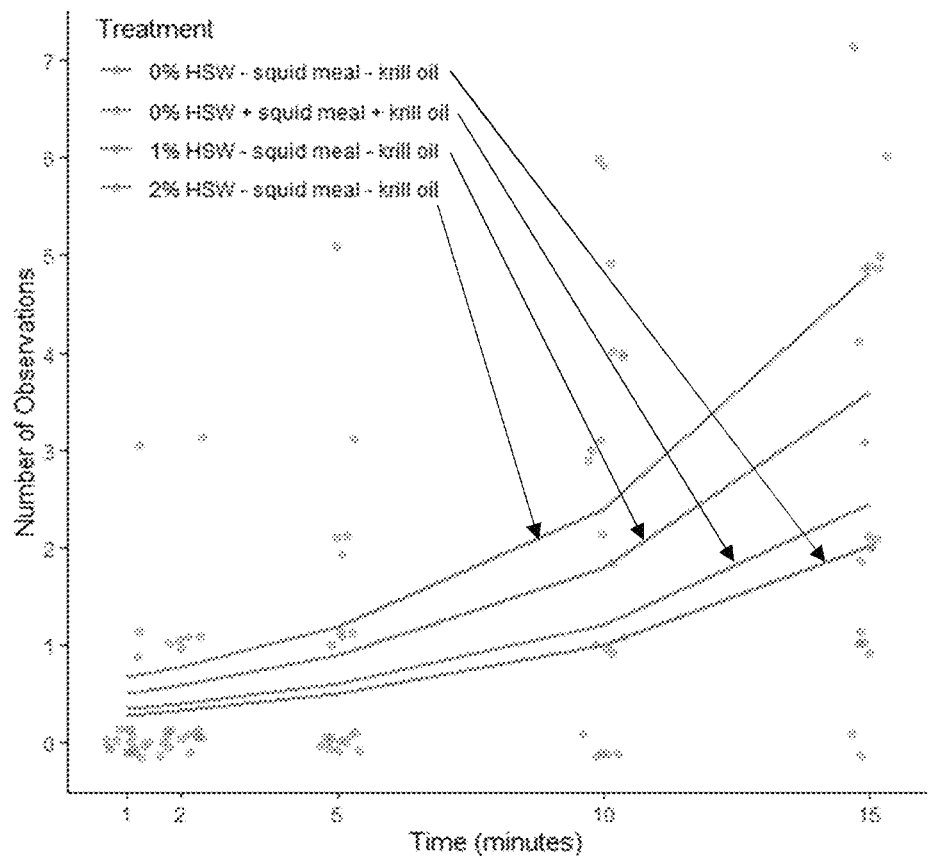
B
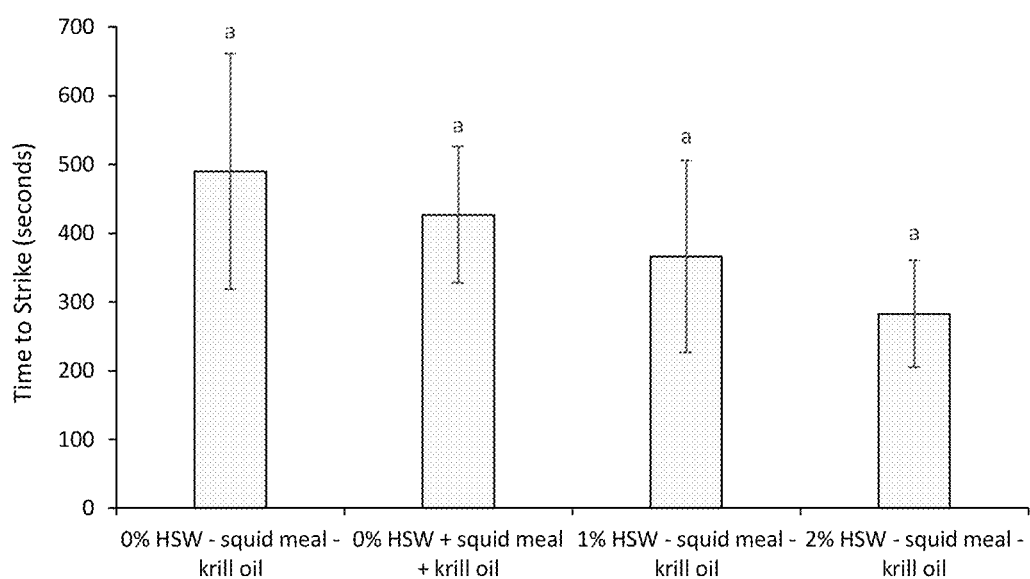

HYDROLYSATE OF WATER SOLUBLE INSECT PROTEINS AND METHOD FOR PREPARATION THEREOF

TECHNICAL FIELD

The present invention relates to a method for producing enzymatically hydrolysed water-soluble insect proteins. In addition, the present invention relates to enzymatically hydrolysed water-soluble insect proteins and to Maillard reaction products of enzymatically hydrolysed water-soluble insect proteins. Furthermore, the present invention relates to the use of the enzymatically hydrolysed water-soluble insect proteins or to the use of the Maillard reaction products of enzymatically hydrolysed water-soluble insect proteins. Finally, the present invention relates to a pet food product, a pet food ingredient, an animal feed product or an animal feed ingredient comprising, or consisting of, the enzymatically hydrolysed water-soluble insect proteins or the Maillard reaction products of enzymatically hydrolysed water-soluble insect proteins, and relates to a human food product or a human food ingredient comprising, or consisting of, the enzymatically hydrolysed water-soluble insect proteins or the Maillard reaction products of enzymatically hydrolysed water-soluble insect proteins.

BACKGROUND

Flavour plays the key role in acceptance of food by animals (Clark, 1998; Dong et al., 2016; Kato et al., 1989). Amongst other identified compounds, free amino acids and peptides based flavour are popularly used to enhance food flavour. Combination of free amino acids or there assembly in short peptides give rise to specific flavour (Kato et al., 1989).

Meat protein hydrolysate and marine protein hydrolysate are commonly used in pet food formulations and in aquaculture feed formulations for the purpose of enhancing flavour. Depending on the method of production, such protein hydrolysates may referred to either as 'digests' (obtained by enzymatic hydrolysis) or as 'palatant' (obtained by enzymatic hydrolysis followed by a second flavour production step, such as for example, subjecting (hydrolysed) protein to a Maillard reaction) (Anuar et al, 2017). Apart from the flavour enhancement, protein hydrolysates may have high digestibility (Everson, 2008) and may have several health promoting properties (Senevirathne and Kim, 2012). Protein hydrolysates are particularly beneficial for rearing young animals that have immature digestive tract and immune systems. Free amino acids and (short) peptides are easy to digest and are readily taken up by their body (Hou et al., 2017).

Protein hydrolysis is a relatively complex process when controlling and steering aspects such as appealing and constant taste, smell, flavour and palatability are considered. Subjecting proteins to hydrolysis can result in development of off-flavours, poor functionality and other factors making the product commercially non-viable (Wisuthiphaet et al., 2016). However, products like hydrolysed krill meal is used in aquaculture and pet food without any off-flavour problems (Tantikitti, 2014). Unfortunately, overfishing has significantly reduced the population of Antarctic Krill (PEW Charitable Trusts, 2014). Provision of suitable replacement products is often a cumbersome challenge, if achievable at all.

Most hydrophobic L-amino acids taste bitter (Kato et al., 1989). In several cases enzymatic hydrolysis of proteins (specially using endopeptidases) render free amino acids or small peptides that contribute to a bitter taste of the product obtained after hydrolysis, which infers a significant disadvantage. For such products, food-processing industry has to employ additional di-bittering steps (e.g. enzymatic bi-bittering) (Tchorbanov et al, 2011) that not only contributes to cost and complexity of the end product, but also alters the flavour profile of the end product.

Insects are commonly consumed as food in many cultures around the world. In European countries, insect proteins are gaining rapid acceptance as high value protein ingredients in animal diets. The European Union has already approved the inclusion of insect proteins in pet food and aquaculture feed formulations. Chicken meal and fish meal are common ingredients in pet food and aquaculture feed preparations, respectively. Insect proteins are increasingly being viewed as an alternative to chicken meal and fish meal in these markets. Amongst all the insect being produced on industrial scale, black soldier fly (*Hermetia illucens*) larvae has gained special attention due to its ability to grow on wide range of organic residues and unique nutritional composition. The nutritional suitability of black soldier fly larvae (BSF) proteins in aquaculture and pet diets is well established.

Pets develop wide range of health disorders with age. Aging can accelerate the free radical damage in a pet's body which might lead to cognitive and locomotor system malfunctioning. Similarly oxidative stress in fishes as a result of immune response could lead to compromised health. Neutrophils (white blood cells) are responsible for the primary defense mechanism of the body. Upon receiving the signal, neutrophils rush to the site of intrusion by pathogenic microbes. Neutrophils then inactive the pathogens by phagocytosis and release of reactive oxygen species (ROS). Production of ROS is crucial for the host defense. However, in the long term, excessive ROS production by neutrophils could damage animal cells and might lead to cellular aging, cancer, reduced immunity, etc.. Dietary interventions that can scavenge ROS may help in reducing oxidative damage in the animal body and resulting health conditions. The field is in need of such dietary interventions.

Therefore, a solution still needs to be found that allows for replacement of for example krill-based protein hydrolysates and hydrolysates derived from different (scarce) protein resources, for protein hydrolysates that have at least similar quality characteristics when taste, flavour, smell, palatability is for example considered. The invention is also aimed at provision of food and feed ingredients obtained from insects, wherein the ingredients have beneficial health properties.

SUMMARY

The present invention seeks to provide a solution to the increasing need for replacement products suitable for replacing current commonly applied protein hydrolysates such as krill-protein based hydrolysate, meat protein derived hydrolysate, fish-protein hydrolysate, etc. In addition, the present invention seeks to provide a solution to the increasing demand for meat substitute products and meat replacement products, for applications in a meat-free diet and for applications relating to reducing production and consumption of meat derived from for example farming and aquaculture.

According to the present invention, a protein hydrolysate as defined above is provided, in which the source of the protein are insect proteins such as proteins isolated from *Hermetia illucens* insect biomass such as proteins derived from black soldier fly, in particular proteins obtained from black soldier fly larvae as the protein source.

Insects are now being considered as a novel source of food proteins and feed proteins (Smetana et al, 2019). Insects like black soldier fly larvae are feed for example on by-products from agro industries and are destined to play an important role in a circular economy. The larvae for example can upcycle agro by-products into valuable source of proteins and lipids. In particular, black soldier fly larvae are able to upcycle agro by-products into valuable source of proteins and lipids, wherein those agro by-products are not suitable as a source of feed for conventional livestock. Commonly, such insects contain relatively high amounts of protein and therewith amino acids (both essential amino acids and non-essential amino acids). Therefore, according to aspects of the invention, such insect-based protein sources serve as raw materials for production of insect protein hydrolysates, in particular when black soldier fly larvae are applied as the protein source. For example, proteins derived from larvae of black soldier fly are suitable for provision of a protein hydrolysate suitable for replacing for example krill-protein based hydrolysates in current pet food applications. For example, several insects, including black soldier fly, contain more than 60% proteins, which is relatively high when compared to the protein content of for example soy bean (40%), beef (40%) and chicken (55%), on a dry matter basis (Paul et al., 2016). Here, the listed protein content percentages relate to the combined essential- and non-essential amino acids content percentages. The current inventors now realized that applying insect-derived proteins as a source for providing protein hydrolysates, is a valuable approach that addresses many of the current problems with today's common hydrolysates (declining natural resources; cumbersome production and controlling of stable-quality products, to name a few drawbacks of current practice). Thus, due to the present invention, the potential of insects as a source for insect-protein based hydrolysates is turned into exploration opportunities.

The current invention therefore relates amongst several further aspects to a method of production of insect protein hydrolysates, wherein protein is obtained from insects like black soldier fly larvae, mealworms, crickets and locusts, in particular obtained from black soldier fly larva as the protein source; to feed ingredient compositions and food ingredient compositions comprising the hydrolysate product obtained with or obtainable by the method of the invention; and applications of such compositions in for example preparing pet food, animal feed, food products for human consumption.

A first aspect of the invention relates to a method for producing an enzymatically hydrolysed water-soluble insect protein, the method comprising the steps of:
a) providing an aqueous water-soluble insect protein composition comprising at least one water-soluble protein, wherein the pH of said composition is between pH 4 and pH 8 and wherein the at least one water-soluble protein in said water-soluble protein composition is solubilized, and further providing at least one peptidase;
b) mixing the at least one peptidase of step a) with the aqueous water-soluble insect protein composition of step a), therewith providing a protein/peptidase mixture;
c) heating the protein/peptidase mixture of step b) at a temperature of below 75° C. such that the at least one water-soluble protein in the protein/peptidase mixture is enzymatically hydrolysed by the at least one peptidase, therewith providing enzymatically hydrolysed protein/peptidase solution; and
d) terminating the enzymatic hydrolysis in the hydrolysed protein/peptidase solution of step c) by heating the hydrolysed protein/peptidase solution at a temperature of between 75° C. and 110° C., such that the at least one peptidase is heat-inactivated by the heating, therewith providing the enzymatically hydrolysed water-soluble insect protein.

Typically, the aqueous water-soluble insect protein composition is derived from black soldier fly larvae as the protein source. It is suitable if the black soldier fly larvae are between 12 and 30 days of age, preferably between 14 and 28 days, more preferably 14-26 days, most preferably 12 hours-3 days before the larvae transform into prepupae, such as 1-2 days before transformation, when the black soldier fly larvae are subjected to a protein extraction means and method, for enabling the provision of the aqueous water-soluble insect protein composition of step a) of the method of the invention.

According to the invention, for example minced black soldier fly larvae meat is applied as a source of a water-soluble insect protein composition, provided in an aqueous solution. It is beneficial when the average particle size of the remains of the minced insects range between 10 and 500 micron. The aqueous water-soluble insect protein composition is for example a water-soluble insect protein composition obtained from black soldier fly larvae by applying the method for isolating a proteinaceous fraction from black soldier fly larvae as described in European patent application EP2953487, in the Examples section thereof, in particular Example 1, page 12, line 8-13 and page 13, line 3-5. In some embodiments, the enzymatically hydrolysed water-soluble insect protein provided by the method of the invention is subjected to a Maillard reaction by heating the protein hydrolysate in the presence of added carbohydrate. However, it is preferred when the aqueous water-soluble insect protein composition that is provided in step a) of the method of the invention is a water-soluble insect protein composition obtained from black soldier fly larvae by applying the following larvae processing method steps (i)-(vi) for isolating a proteinaceous fraction from black soldier fly larvae:
(i) providing black soldier fly larvae, preferably black soldier fly larvae 12-30 days of age, preferably 14-28 days, more preferably 14-26 days, most preferably 12 hours-3 days before the larvae transform into prepupae, such as 1-2 days before transformation,
(ii) reducing the black soldier fly larvae of step (i) in size, preferably by mincing, wherein the average particle size of the remains of the insects in the pulp of step a) ranges between 10 micron and 500 micron, then
(iii) obtaining a pulp from the insects with reduced size of step (ii), then
(iv) heating the pulp of step (iii) to a temperature of 80-95° C., preferably to a temperature of 85-92° C., heating preferably for a time period of 70 seconds-100 seconds, more preferably 75 seconds-90 seconds, then
(v) subjecting the heated pulp of step (iv) to a physical separation step, preferably encompassing decanting and/or centrifugation, thereby providing the insect protein composition, and then
(vi) mixing the insect protein composition of step (v) in water or an aqueous buffer, preferably water, therewith providing the aqueous water-soluble insect protein composition of step a) of the method for producing an enzymatically hydrolysed water-soluble insect protein according to the invention.

The inventors established that by applying this larvae processing method steps as part of the method of the invention, in step a) of the method, a protein pulp obtained from black soldier fly larvae as the protein source, is obtained which pulp has surprisingly improved features and structural characteristics, when compared to pulp obtained from such larvae by applying an alternative black soldier fly larvae processing method known in the art, such as the method outlined in European patent application EP2953487, in the Examples section thereof, in particular Example 1, page 12, line 8-13 and page 13, line 3-5. In particular, the relatively short heating time of less than 100 seconds, in step (iv) of the method of the invention, is deemed essential for obtaining improved larvae pulp. It has been found by the inventors that by using the time-temperature combination less oil is entrapped within the protein fraction, therewith providing a more pure protein source in step a) of the method of the invention, compared with protein sources provided using alternative, current means and methods for isolating protein pulp from black soldier fly larvae as the protein source. It has also been found that discolouration of the pulp (of protein) due to Maillard reactions is largely avoided, thereby improving the quality of the product obtained. For example, protein with reduced fat content is obtained when minced black soldier fly larvae are heated for 80 seconds at 90° C., or for 75-85 seconds at a temperature of 90° C.±2° C. In EP2953487, heating time is at least 5 minutes and even 30 minutes. Furthermore, the relatively short heating time of at most 100 seconds, preferably about 70-90 seconds, of the minced black soldier fly pulp results in less granulated and less aggregated insect pulp compared to longer heating times applied in current methods known in the art. Less granulated larvae pulp is beneficial for the enzymatic hydrolysis of the protein comprised by the pulp. Granulation reduces enzyme efficiency since the particulate matter is less accessible for the enzyme molecules. By applying the larvae processing method steps as part of the method of the invention, the short heating time results in a protein composition consisting of smaller protein clusters, aggregates, particles, or even (mainly) of protein monomers and/or small multimers, compared with the larger protein aggregates and particles obtained when black soldier fly larvae pulp is subjected to heating for over 100 seconds such as for 5 minutes up to 30 minutes.

A second aspect of the invention relates to an enzymatically hydrolysed water-soluble insect protein obtained by the method of the invention, or an enzymatically hydrolysed water-soluble insect protein obtainable by the method of the invention, or relates to Maillard reaction products of enzymatically hydrolysed water-soluble insect protein obtained by the method of the invention, or relates to Maillard reaction products of enzymatically hydrolysed water-soluble insect protein obtainable by the method of the invention.

A third aspect of the invention relates to enzymatically hydrolysed water-soluble insect protein or Maillard reaction products of enzymatically hydrolysed water-soluble insect protein, wherein at least 50% of said protein has a molecular weight of less than 1,000 Dalton, based on the total weight of said protein, preferably 55%-100%, more preferably 65%-100%, most preferably 75%-100%, such as 80%-95% or 85%-100% or 85%-90%.

A fourth aspect of the invention relates to the use of the enzymatically hydrolysed water-soluble insect protein or the Maillard reaction products of enzymatically hydrolysed water-soluble insect protein of the invention in the production of a pet food product, a pet food ingredient, an animal feed product or animal feed ingredient, or in the production of a human food product or human food ingredient.

A fifth aspect of the invention relates to an animal feed product or an animal feed ingredient or a pet food product or a pet food ingredient comprising, or consisting of, the enzymatically hydrolysed water-soluble insect protein or the Maillard reaction products of enzymatically hydrolysed water-soluble insect protein of the invention, or a human food product or a human food ingredient comprising, or consisting of, the enzymatically hydrolysed water-soluble insect protein or the Maillard reaction products of enzymatically hydrolysed water-soluble insect protein of the invention.

A sixth aspect of the invention relates to use of the enzymatically hydrolysed water-soluble insect protein or the Maillard reaction products of enzymatically hydrolysed water-soluble insect protein of the invention as an antioxidant. In particular, as a food or feed ingredient with antioxidant activity. The enzymatically hydrolysed water-soluble insect protein and the Maillard reaction products of enzymatically hydrolysed water-soluble insect protein of the invention thus have antioxidant properties.

A seventh aspect of the invention relates to use of the animal feed product or the animal feed ingredient or the pet food product or the pet food ingredient of the invention as an antioxidant and/or as an ingredient with health promoting potential.

An aspect of the invention relates to the animal feed product or the animal feed ingredient or the pet food product or the pet food ingredient of the invention for use in a method for the prevention and/or suppression of cellular oxidative damage.

A further aspect of the invention relates to an animal feed product or an animal feed ingredient or a pet food product or a pet food ingredient comprising the enzymatically hydrolysed water-soluble insect protein or the Maillard reaction products of enzymatically hydrolysed water-soluble insect protein of the invention with antioxidant activity according to the invention. The antioxidant activity of the animal feed product or the animal feed ingredient or the pet food product or the pet food ingredient comprising the enzymatically hydrolysed water-soluble insect protein or the Maillard reaction products of enzymatically hydrolysed water-soluble insect protein is due to the antioxidant properties of the enzymatically hydrolysed water-soluble insect protein or the Maillard reaction products of enzymatically hydrolysed water-soluble insect protein of the invention.

SHORT DESCRIPTION OF DRAWINGS

The present invention will be discussed in more detail below, with reference to the attached drawings, in which FIG. 1. (FIG. 1) displays a production flow chart for producing protein hydrolysate from an aqueous water-soluble protein composition derived from black solider fly larvae; and FIG. 2. (FIG. 2) Target limits and critical limits for microbial counts in products suitable for human consumption.

Figure 3:
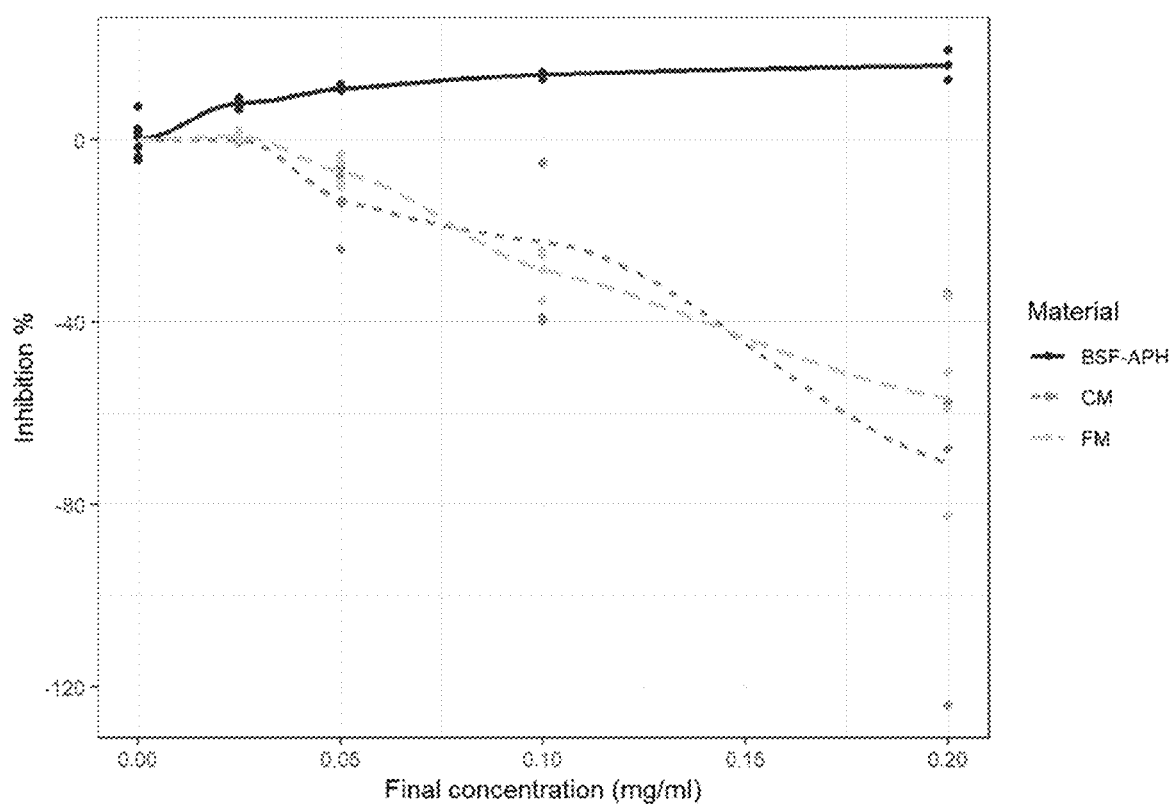

FIG. 3. (FIG. 3) DPPH radical scavenging activity of BSF aqueous protein hydrolysate (BSF-APH), Chicken meal (CM) and Fish meal (FM) after 30 min incubation (n=3).

Figure 4:
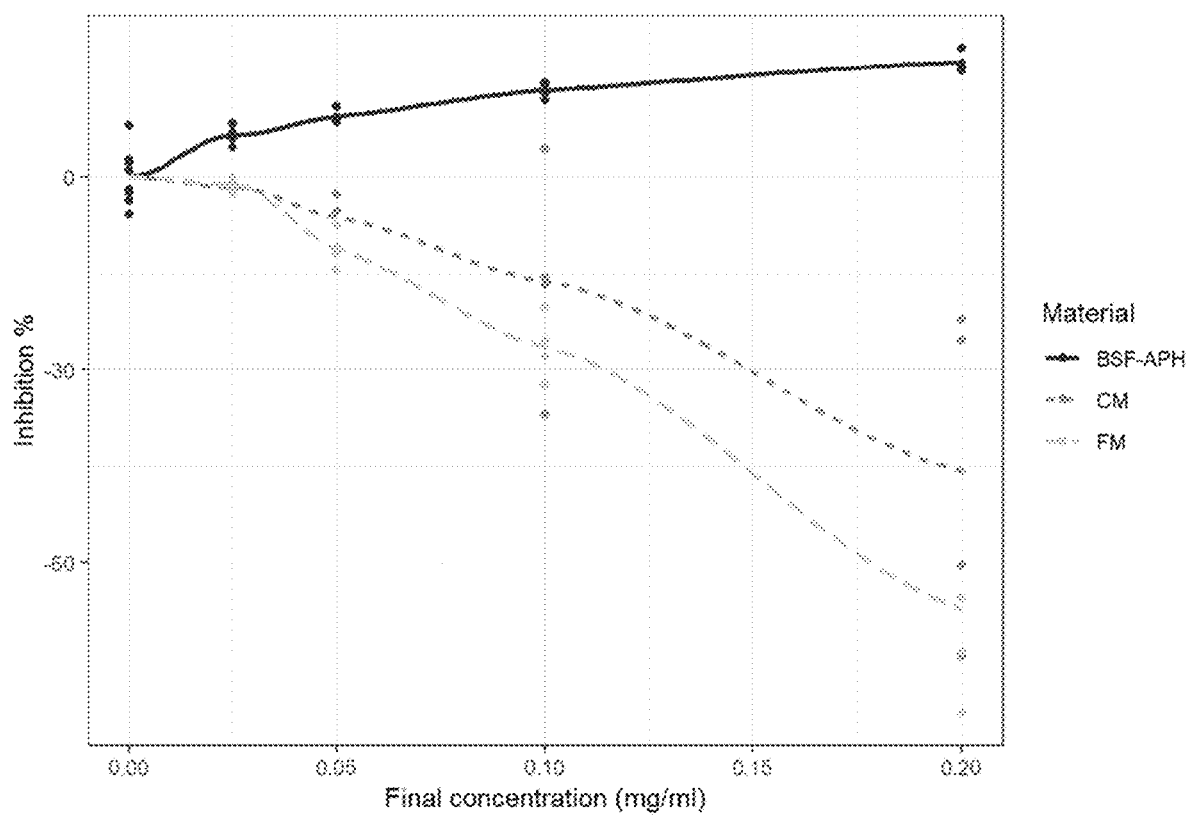

FIG. 4: (FIG. 4) DPPH radical scavenging activity of BSF aqueous protein hydrolysate (BSF-APH), Chicken meal (CM) and Fish meal (FM) after 60 min incubation (n=3).

Figure 5:
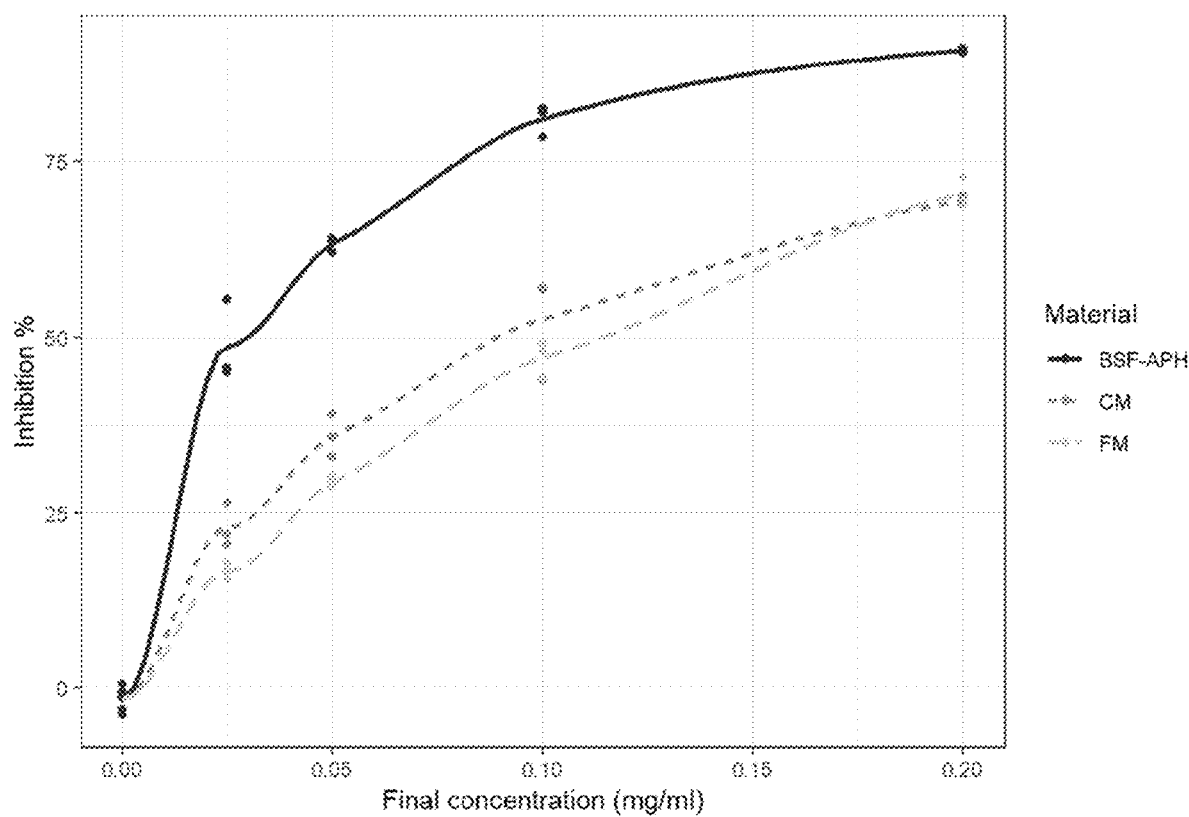

FIG. 5: (FIG. 5) ABTS cation radical scavenging activity of BSF aqueous protein hydrolysate (BSF-APH), Chicken meal (CM) and Fish meal (FM) after 30 min incubation (n=3).

Figure 6:
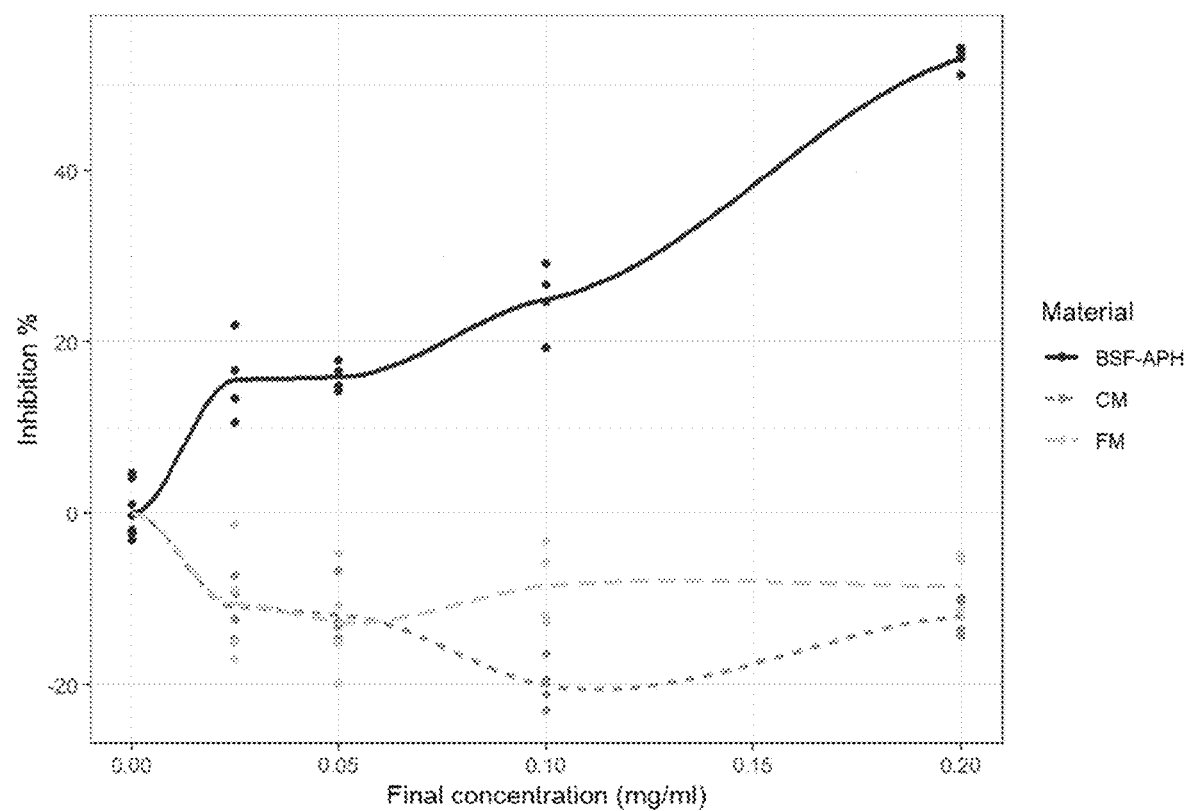

FIG. 6: (FIG. 6) MPO response modulation activity of BSF aqueous protein hydrolysate (BSF-APH), Chicken meal (CM) and Fish meal (FM) using SIEFED assay (n=3).

Figure 7:
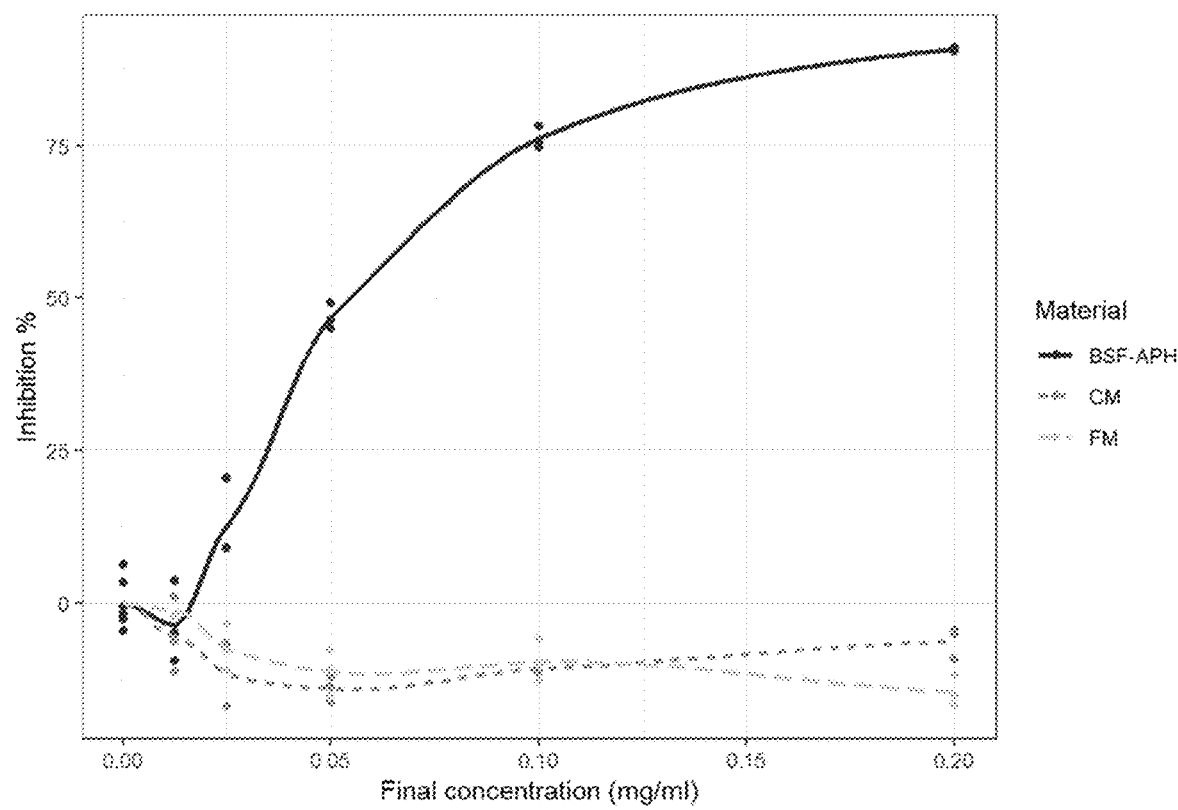

FIG. 7: (FIG. 7) MPO response modulation activity of BSF aqueous protein hydrolysate (BSF-APH), Chicken meal (CM) and Fish meal (FM) using classical measurement (n=3).

Figure 8:
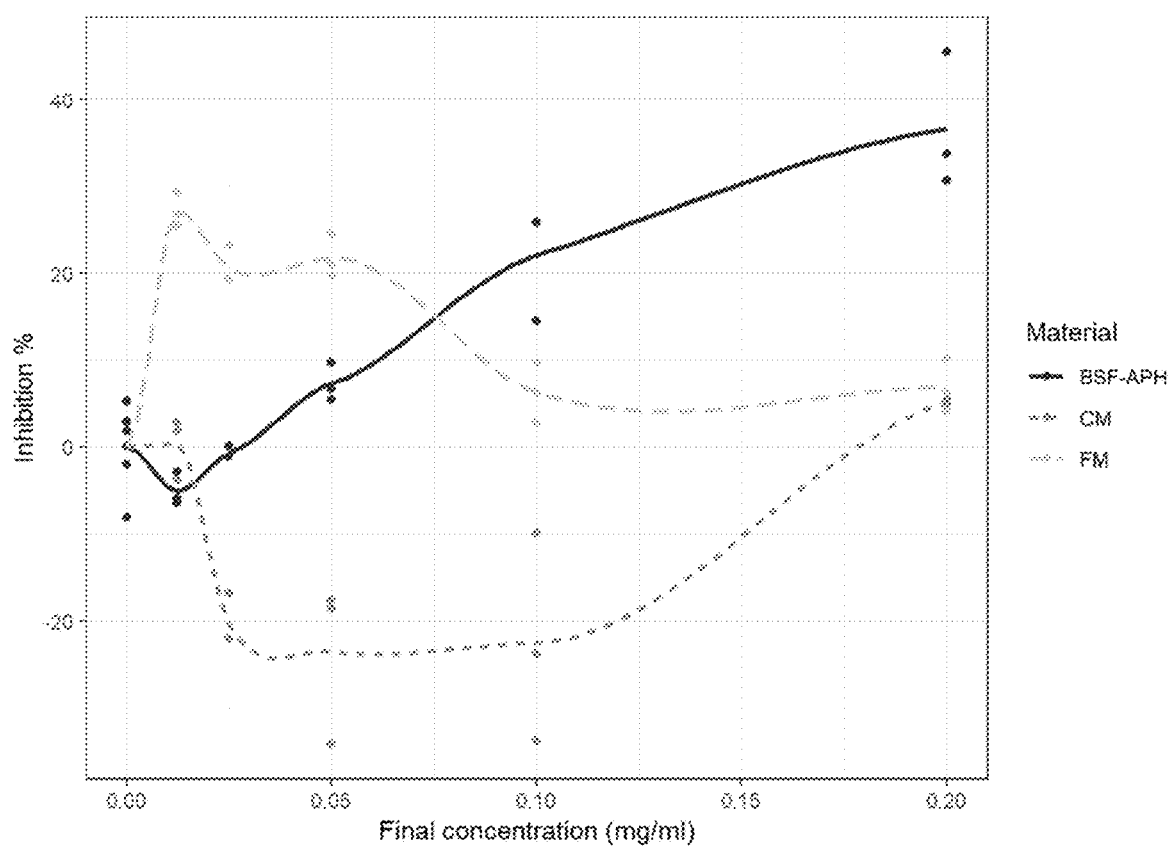

FIG. 8: (FIG. 8) Neutrophil response modulation activity of BSF aqueous protein hydrolysate (BSF-APH), Chicken meal (CM) and Fish meal (FM) (n=3).

FIG. 9A (FIG. 9A). Dog food palatability testing (0.5% HIE 2).

FIG. 9B (FIG. 9B). Dog food palatability testing (1.25% HIE 2).

FIG. 9C (FIG. 9C). Dog food palatability testing (2.50% HIE 2).

FIG. 10A (FIG. 10A): Jittered count observations at each time interval with the predicted performance fit for each diet over time (indicated with an arrow).

FIG. 10B (FIG. 10B): Time to strike. Average length of time for one shrimp to begin feeding on a diet, showing standard error. Different superscript letters demonstrate where statistically significant differences were noted between diet groups (p<0.05).

DESCRIPTION OF EMBODIMENTS

It is a first goal of the present invention to provide an improved method for providing protein hydrolysate. It is a second goal of the present invention to provide a substitute product for current protein hydrolysate, wherein the substitute product is more sustainable compared to current protein hydrolysates.

It is an objective of the current invention to provide a more sustainable method for producing protein hydrolysate, therewith providing a more sustainable protein hydrolysate, yet a protein hydrolysate that at least meets the quality measures and characteristics that allows the application of the protein hydrolysate as a replacement product for current protein hydrolysates, such as those protein hydrolysates currently applied in production of for example pet food, human food ingredients, livestock feed or aquaculture feed.

At least one of the above objectives is achieved by providing an insect-based protein hydrolysate of the invention.

The present invention will be described with respect to particular embodiments but the invention is not limited thereto but only by the claims.

Furthermore, the terms first, second, third and the like in the description and in the claims, are used for distinguishing between for example similar elements, constituents in a composition, or separate method steps, and not necessarily for describing a sequential or chronological order. The terms are interchangeable under appropriate circumstances and the embodiments of the invention can operate in other sequences than described or illustrated herein, unless specified otherwise.

The embodiments of the invention described herein can operate in combination and cooperation, unless specified otherwise.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to for example the elements or the method steps or the constituents of a compositions listed thereafter; it does not exclude other elements or method steps or constituents in a certain composition. It needs to be interpreted as specifying the presence of the stated features, integers, (method) steps or components as referred to, but does not preclude the presence or addition of one or more other features, integers, steps or components, or groups thereof. Thus, the scope of the expression "a method comprising steps A and B" should not be limited to a method consisting only of steps A and B, rather with respect to the present invention, the only enumerated steps of the method are A and B, and further the claim should be interpreted as including equivalents of those method steps. Thus, the scope of the expression "a composition comprising components A and B" should not be limited to a composition consisting only of components A and B, rather with respect to the present invention, the only enumerated components of the composition are A and B, and further the claim should be interpreted as including equivalents of those components.

In addition, reference to an element or a component by the indefinite article "a" or "an" does not exclude the possibility that more than one of the element or component are present, unless the context clearly requires that there is one and only one of the elements or components. The indefinite article "a" or "an" thus usually means "at least one".

A first aspect of the invention relates to a method for producing an enzymatically hydrolysed water-soluble insect protein, the method comprising the steps of:

a) providing an aqueous water-soluble insect protein composition comprising at least one water-soluble protein, wherein the pH of said composition is between pH 4 and pH 8 and wherein the at least one water-soluble protein in said water-soluble protein composition is solubilized, and further providing at least one peptidase;

b) mixing the at least one peptidase of step a) with the aqueous water-soluble insect protein composition of step a), therewith providing a protein/peptidase mixture;

c) heating the protein/peptidase mixture of step b) at a temperature of below 75° C. such that the at least one water-soluble protein in the protein/peptidase mixture is enzymatically hydrolysed by the at least one peptidase, therewith providing enzymatically hydrolysed protein/peptidase solution; and d) terminating the enzymatic hydrolysis in the hydrolysed protein/peptidase solution of step c) by heating the hydrolysed protein/peptidase solution at a temperature of between 75° C. and 110° C., such that the at least one peptidase is heat-inactivated by the heating, therewith providing the enzymatically hydrolysed water-soluble insect protein.

Typically, the aqueous water-soluble insect protein composition is derived from black soldier fly larvae as the protein source. It is suitable if the black soldier fly larvae are between 12 and 30 days of age, preferably between 14 and 28 days, more preferably 1426 days, most preferably 12 hours-3 days before the larvae transform into prepupae, such as 1-2 days before transformation, when the black soldier fly larvae are subjected to a protein extraction means and method, for enabling the provision of the aqueous water-soluble insect protein composition of step a) of the method of the invention.

According to the invention, for example minced black soldier fly larvae meat is applied as a source of a water-soluble insect protein composition, provided in an aqueous solution. It is beneficial when the average particle size of the remains of the minced insects range between 10 and 500 micron. The aqueous water-soluble insect protein composition is for example a water-soluble insect protein composition obtained from black soldier fly larvae by applying the method for isolating a proteinaceous fraction from black soldier fly larvae as described in European patent application EP2953487, in the Examples section thereof, in particular Example 1, page 12, line 8-13 and page 13, line 3-5. In some embodiments, the enzymatically hydrolysed water-soluble insect protein provided by the method of the invention is subjected to a Maillard reaction by heating the protein hydrolysate in the presence of added carbohydrate. However, it is preferred when the aqueous water-soluble insect protein composition that is provided in step a) of the method of the invention is a water-soluble insect protein composition obtained from black soldier fly larvae by applying the following larvae processing method steps (i)-(vi) for isolating a proteinaceous fraction from black soldier fly larvae:
  (i) providing black soldier fly larvae, preferably black soldier fly larvae 12-30 days of age, preferably 14-28 days, more preferably 14-26 days, most preferably 12 hours-3 days before the larvae transform into prepupae, such as 1-2 days before transformation,
  (ii) reducing the black soldier fly larvae of step (i) in size, preferably by mincing, wherein the average particle size of the remains of the insects in the pulp of step a) ranges between 10 micron and 500 micron, then
  (iii) obtaining a pulp from the insects with reduced size of step (ii), then
  (iv) heating the pulp of step (iii) to a temperature of 80-95° C., preferably to a temperature of 85-92° C., heating preferably for a time period of 70 seconds-100 seconds, more preferably 75 seconds-90 seconds, then
  (v) subjecting the heated pulp of step (iv) to a physical separation step, preferably encompassing decanting and/or centrifugation, thereby providing the insect protein composition, and then
  (vi) mixing the insect protein composition of step (v) in water or an aqueous buffer, preferably water, therewith providing the aqueous water-soluble insect protein composition of step a) of the method for producing an enzymatically hydrolysed water-soluble insect protein according to the invention.

The inventors established that by applying this larvae processing method steps as part of the method of the invention, in step a) of the method, a protein pulp obtained from black soldier fly larvae as the protein source, is obtained which pulp has surprisingly improved features and structural characteristics, when compared to pulp obtained from such larvae by applying an alternative black soldier fly larvae processing method known in the art, such as the method outlined in European patent application EP2953487, in the Examples section thereof, in particular Example 1, page 12, line 8-13 and page 13, line 3-5. In particular, the relatively short heating time of less than 100 seconds, in step (iv) of the method of the invention, is deemed essential for obtaining improved larvae pulp. It has been found by the inventors that by using the time-temperature combination less oil is entrapped within the protein fraction, therewith providing a more pure protein source in step a) of the method of the invention, compared with protein sources provided using alternative, current means and methods for isolating protein pulp from black soldier fly larvae as the protein source. It has also been found that discolouration of the pulp (of protein) due to Maillard reactions is largely avoided, thereby improving the quality of the product obtained. For example, protein with reduced fat content is obtained when minced black soldier fly larvae are heated for 80 seconds at 90° C., or for 75-85 seconds at a temperature of 90° C.±2° C. In EP2953487, heating time is at least 5 minutes and even 30 minutes. Furthermore, the relatively short heating time of at most 100 seconds, preferably about 70-90 seconds, of the minced black soldier fly pulp results in less granulated and less aggregated insect pulp compared to longer heating times applied in current methods known in the art. Less granulated larvae pulp is beneficial for the enzymatic hydrolysis of the protein comprised by the pulp. Granulation reduces enzyme efficiency since the particulate matter is less accessible for the enzyme molecules. By applying the larvae processing method steps as part of the method of the invention, the short heating time results in a protein composition consisting of smaller protein clusters, aggregates, particles, or even (mainly) of protein monomers and/or small multimers, compared with the larger protein aggregates and particles obtained when black soldier fly larvae pulp is subjected to heating for over 100 seconds such as for 5 minutes up to 30 minutes.

For the method according to the invention, it is preferred that the aqueous water-soluble insect protein composition of step a) comprises more than one water-soluble protein, preferably more than two different water-soluble proteins, more preferably more than three different water-soluble proteins, most preferably more than four different water-soluble proteins. According to the invention, any number of the different water-soluble proteins present in an insect can be selected for the aqueous water-soluble insect protein composition provided in step a) of the method. Therefore, it is also part of the invention that all water-soluble proteins present in an insect are part of the aqueous water-soluble insect protein composition provided in step a) of the method. Alternatively, a selected number of proteins and/or a selected set of specific proteins encompassing at least one water-soluble insect protein, can be provided in step a) of the method of the invention as the aqueous water-soluble insect protein composition comprising at least one water-soluble protein. Preferred is a water-soluble protein composition comprising all water-soluble insect proteins derived from an insect source. For example, the aqueous water-soluble insect protein composition comprising at least one water-soluble protein provided in step a) of the method of the invention is a protein composition derived from minced insect meat or pure such as black soldier fly meat or preferably minced black soldier fly larvae meat, according to the invention. It is preferred that the aqueous water-soluble insect protein composition comprising at least one water-soluble protein provided in step a) of the method of the invention, is a protein composition obtained from black soldier fly larvae. Typically, these larvae are 14-24 days of age, such as 19-22 days of age. Typically, such black soldier fly larvae contain about 35% by weight to 65% by weight protein based on the total mass of said larvae.

In particular, in the method according to the invention, in step c) the heating is at a temperature of between 35° C. and 60° C., and/or the heating is for a duration of between 2 hours and 12 hours, and in the method of the invention preferably in step c) the heating is at a temperature of between 35° C. and 60° C. for a duration of between 2 hours and 12 hours. For example, the method of the invention is applied, wherein the heating in step c) was at 45° C. or at 55° C., and the heating during step c) of the method was for 4 hours or for 8 hours. Typically, the temperature during the heating step c) of the method was 50° C. and typically the heating time was 6 hours. The pH during the heating step c) of the method of the invention is preferably between pH 6 and 8, and typically the pH is 6,5-7,5, preferably 6,8-7,2, such as pH 7. An embodiment is the method of the invention wherein in step c) the heating temperature is 50° C., the heating time in step c) is 6 hours and the pH is 7. Embodiments of the invention, wherein these process conditions were applied in the method according to the invention are further exemplified in the Examples section. The skilled person appreciates that the combination of heating time, temperature at which the enzymatic hydrolysis step c) is performed and the pH of the aqueous solution of water-soluble protein, are three parameters that are selected and optimized for the purpose of efficient protein hydrolysis. That is to say, for a selected protein-hydrolysing enzyme, optimum pH conditions, temperature optimum with regard to enzymatic activity, and a suitable reaction time when the desired extend of the enzymatic hydrolysis of the proteins is considered, is selected for the method of the invention. Particularly, it is part of the invention that the pH of the aqueous water-soluble protein composition is such that the enzymatic hydrolysis is proceeding efficiently within the reaction time, according to the invention. Similarly, the heating temperature is selected such that the protein-hydrolysing enzyme hydrolysis efficiently within the chosen reaction time. In addition, the selected time for the enzymatic hydrolysis step is chosen to last as long as suitable in order to provide essentially the highest achievable fraction of hydrolysed protein, when the combination of selected enzyme, hydrolysis temperature, enzyme concentration, pH and hydrolysis time is considered. Selecting the suitable combination of pH, enzyme concentration, heating temperature for hydrolysis, and reaction time for the hydrolysis step, as such is part of the invention when the enzymatic hydrolysis of insect proteins is considered. To the surprise of the inventors, by applying the method of the invention water soluble insect proteins are efficiently hydrolysed at near-neutral pH or neutral pH, within a relatively short time, to a relatively high extent. That is to say, providing a water-soluble insect protein composition such as black soldier fly larvae proteins, and subjecting said protein composition to the hydrolysis method of the invention at pH 7 for about 6 hours at about 50° C. for the step of enzymatic hydrolysis, resulted in hydrolysed protein comprising over 85% by weight proteins with a molecular weight of less than 1000 Dalton, such as over 90%, over 95%, and in embodiments up to 100% based on the total weight of the proteins, and in a pepsin digestibility of 100%. In addition, the content of free amino-acid residues is typically over 30% such as over 40% by weight based on the total weight of the protein. Thus, to the surprise of the inventors, the pepsin digestibility of insect proteins such as black soldier larvae proteins, is extremely high, i.e. 100%, and in addition the content of free amino-acid residues after the method step of enzymatically digesting the insect protein is also relatively high: as high as 34%-50% or 40%-50% by weight based on the total weight of the protein, when black soldier fly larvae proteins are considered. See also the Examples section.

An embodiment is the method according to the invention, wherein in step c) of the method the heating is at a temperature of between 40° C. and 55° C., and/or wherein the heating is for a duration of between 4 hours and 9 hours, preferably in step c) the heating is at a temperature of between 40° C. and 55° C. for a duration of between 4 hours and 9 hours, more preferably, in step c) the heating is at a temperature of between 45° C. and 53° C. for a duration of between 5 hours and 7 hours, most preferably, the heating is at a temperature of 50° C. for a duration of 6 hours.

In embodiments, the method according to the invention comprises the step a), wherein in said step a) the pH of the aqueous water-soluble insect protein composition is between 5 and 7,7, preferably between 6 and 7,5, more preferably the pH is 7,0. Water-soluble insect proteins are particularly stable in an aqueous solution at a pH of about 7. The inventors established that an aqueous water-soluble insect protein composition which has a pH of about 7, is a suitable source of proteins for efficient and efficacious enzymatic hydrolysis of the proteins, when such proteins are subjected to the method of the invention. The method of the invention provides a robust means for providing hydrolysed proteins with a constant degree of hydrolysis and pepsin digestibility. Herewith, the batch-to-batch variation between hydrolysed insect protein compositions is minimized. With the selected pH, temperature, enzyme dose, hydrolysis time, the method of the invention provides for enzymatically hydrolysed water-soluble insect protein of constant composition, the more since the degree of pepsin digestibility and the content of free amino-acid residues that is achievable with the insect proteins, are high, as indicated, i.e. (near) 100% pepsin digestibility and over 30%, such as over 40% by weight free amino-acid residues based on the total weight of the protein.

An embodiment is the method according to the invention, wherein the at least one peptidase provided in step a) of the method is an amino-peptidase, preferably an endopeptidase or an exopeptidase or a mixture thereof, or wherein the at least one peptidase provided in step a) of the method comprises an amino-peptidase, preferably an endopeptidase or an exopeptidase or a mixture thereof.

It is preferred that in the method according to the invention, in step a) the at least one peptidase comprises, or is selected from leucyl amino-peptidase, papain, pronase, serine protease, alcalase, subtilisin, subtilisin A, α-chymotrypsin, cathepsin III, esperase, neutrase, pepsin, thermolysin, trypsin, and in the method preferably in step a) the at least one peptidase is leucyl amino-peptidase, or in the method preferably in step a) the at least one peptidase comprises leucyl amino-peptidase. The inventors established that in particular the application of at least a leucyl amino-peptidase in the method of the invention is very suitable for the provision of a hydrolysed insect protein composition. For example, the amount of free amino acid residues is over 34% by weight based on the total weight of the protein subjected to the hydrolysis step in the method of the invention, when a leucyl amino-peptidase is applied. Surprisingly, subjecting black soldier fly larvae proteins, i.e. the water-soluble larvae proteins, to the method of the invention, provides a hydrolysed protein composition wherein the amount of peptides with a mass of less than 1000 Dalton is over 85% such as up to 100% by weight based on the total weight of the protein, and in addition, the content of free amino acid residues in the hydrolysed protein is more than 33% such as more than 45% by weight based on the total weight of the proteins. Such high degree of hydrolysis provides a hydrolysed protein composition that is suitable for applications as a food ingredient, a pet food ingredient and an animal feed ingredient, for human consumption, for example feeding cats or dogs, for applications in livestock breeding, farming, aqua culture, etc., etc., for example. The robustness of the method of the invention, together with the high digestibility and the high content of small peptides and free amino-acid residues provides for a suitable source of food and feed flavour and palatant.

Certain embodiments are the method according to the invention, wherein in step b) the amount of the at least one peptidase in the protein/peptidase mixture is between 0.05% and 7% by weight of the total weight of the protein/peptidase mixture, preferably between 0.1% and 6%, more preferably between 0,2% and 5%, most preferably between 0.5% and 3% such as 1,0%-2,0% by weight of the total weight of the protein/peptidase mixture. Typically, such selected amounts of enzyme such as a leucyl amino-peptidase, are suitable for efficient enzymatic hydrolysis of insect proteins such as the water-soluble proteins obtained from black soldier larvae. Typically, the peptidase is present in the method of the invention in an amount suitable for fast and efficient protein hydrolysis, wherein the water-soluble insect protein is provided at a concentration of 2%-25% by weight based on the total weight of the protein composition, preferably 3,5%-20%, such as about 3,8% or about 19%.

An embodiment is the method according to the invention, wherein in step d) the enzymatic hydrolysis in the hydrolysed protein/peptidase solution of step c) is terminated by heating the hydrolysed protein/peptidase solution for a duration of between 30 seconds and 30 minutes, preferably 45 seconds-20 minutes, more preferably 1 minute-15 minutes, most preferably between 2 minutes and 10 minutes.

An embodiment is the method according to the invention, wherein in step d) the enzymatic hydrolysis in the hydrolysed protein/peptidase solution of step c) is terminated by heating the hydrolysed protein/peptidase solution to a temperature of 80° C.-105° C., preferably 85° C.-103° C., more preferably 90° C.-100° C. Typically, the enzyme inactivation step d) of the method of the invention takes 1.5 minutes-8 minutes, and preferably 2 minutes. Typically, the enzyme deactivation step is by heating the hydrolysed protein/peptidase solution in step d) of the method of the invention at 100° C., such as for example for 2 minutes.

An embodiment is the method of the invention, wherein after step d) in an optional further step e) the enzymatically hydrolysed water-soluble insect protein of step d) is subjected to a Maillard reaction for the provision of modified amino groups in said enzymatically hydrolysed protein, the Maillard reaction comprising the sub-steps e1) providing a carbohydrate and mixing the carbohydrate with the enzymatically hydrolysed water-soluble insect protein of step d), therewith providing an enzymatically hydrolysed insect protein/added carbohydrate mixture;

e2) heating the enzymatically hydrolysed insect protein/added carbohydrate mixture of step e1), therewith providing Maillard reaction products of enzymatically hydrolysed insect protein.

An embodiment is the method according to the invention, wherein in the optional step e1) the final concentration of added carbohydrate is between 0.05% and 6,0% by weight of the total weight of the enzymatically hydrolysed insect protein/added carbohydrate mixture, preferably between 0.1% and 5,0%, more preferably between 0,2% and 3%, most preferably 0,3%-1,0% by weight of the total weight of the enzymatically hydrolysed insect protein/added carbohydrate mixture.

Preferably, as part of the method according to the invention, in the optional step e2) the enzymatically hydrolysed insect protein/added carbohydrate mixture of the optional step e1) is heated at a temperature of between 100° C. and 170° C., preferably 120° C.-168° C., more preferably 135° C.-166° C., such as between 140° C. and 165° C. It is preferred that the temperature applied for heating the enzymatically hydrolysed insect protein/added carbohydrate mixture of the optional step e1) is 145° C.-160° C., such as 150° C., 155° C. In preferred embodiments, the temperature during the Maillard reaction is 150° C. The inventors established that applying the heating temperature of 145° C.-155° C., preferably for about 10 minutes-20 minutes, such as 150° C. for 20 minutes, results in Maillard reaction products which have a very attractive and pleasant taste and/or flavour and/or palatability, when the Maillard reaction products, i.e. the Maillard reaction products of enzymatically hydrolysed insect protein, are applied as for example pet food ingredient in cat food and dog food, or as for example a food ingredient in a food product for human use, such as noodles, soup, hamburger, etc.

An embodiment is the method according to the invention, wherein in the optional method step e2) the enzymatically hydrolysed insect protein/added carbohydrate mixture of the optional method step e1) is heated for a time period of between 1 minute and 120 minutes, preferably 2 minutes-60 minutes, more preferably 3 minutes-30 minutes, most preferably 5 minutes-20 minutes, such as 10 minutes-17 minutes or about 15 minutes. The inventors established that heating the enzymatically hydrolysed black soldier fly larvae proteins, that are provided with the method of the invention, for about 15 minutes in the presence of added sucrose or glucose, preferably sucrose or glucose or a mixture thereof at an amount of 0,3%-1,0% by weight of the total weight of the enzymatically hydrolysed insect protein/added carbohydrate mixture that is subjected to the Maillard reaction, resulted in a surprisingly intense and appealing beef-meat like taste or pork-meat like taste. In a blinded test, all individuals in a panel of human subjects unanimously indicated that the taste, flavour and/or palatability of food stuff comprising the protein hydrolysate provided with the method of the invention, or comprising the Maillard reaction products of enzymatically hydrolysed insect protein, was better and exceeded the taste, flavour and/or palatability of food stuff that was not enriched with the insect protein hydrolysate or with the Maillard reaction products of enzymatically hydrolysed insect protein.

An embodiment is the method according to the invention, wherein in the optional method step e1) the provided carbohydrate is sucrose or glucose or a mixture thereof, preferably sucrose. The inventors established that the method of the invention consistently provided Maillard products with an intense meat-like taste and palatability, when water-soluble proteins of black soldier fly larvae were subjected to the method of the invention. The skilled person appreciates that apart from glucose, sucrose or a mixture thereof, further carbohydrates are known for their suitability to bind and react with amino-acid residue side-chains. An example is glucose-6-phosphate. Therefore, it is also part of the invention that in the method of the invention in the optional step e1), other carbohydrates or mixtures thereof, with or without sucrose and/or glucose, such as glucose-6-phosphate, are applied for providing Maillard reaction products of enzymatically hydrolysed insect protein. By including carbohydrates different from sucrose and glucose, or by combining sucrose and/or glucose with at least an other carbohydrate, the method of the invention is suitable for providing Maillard reactions products or advanced glycation end-products of enzymatically hydrolysed insect protein, which have a taste and/or flavour and/or palatability that differs from the Maillard reactions products or advanced glycation end-products of enzymatically hydrolysed insect protein that are obtained when sucrose or glucose is applied in the method. The method of the invention thus provides for the opportunity to control and direct the taste and/or flavour and/or palatability of the enzymatically hydrolysed insect protein subjected to the method, by controlling the type of selected carbohydrate(s), the concentration of the carbohydrate(s) during the optional steps e1) and e2) of the method of the invention, and the heating time and heating temperature during the Maillard reaction. Typically, Arg amino-acid residues are prone to formation of Maillard reaction products and/or advanced glycation end-products.

An embodiment is the method according to the invention, wherein after step d) in an optional further step f1) the enzymatically hydrolysed water-soluble insect protein of step d) is dried, preferably by applying any one or more of spray-drying, drying by fluidized bed drying, lyophilisation, refractive drying. A further embodiment is the method according to the invention, wherein after the optional method step e2) in an optional further step f2) the Maillard reaction products of enzymatically hydrolysed water-soluble insect protein of step e2) is dried, preferably by applying any one or more of spray-drying, drying by fluidized bed drying, lyophilisation, refractive drying. The benefits of providing dried water-soluble insect protein compositions such as the aforementioned water-soluble black soldier fly larvae protein composition, are for example relating to extended shelf life when stock piled, and to the opportunity to prepare an aqueous water-soluble insect protein composition at a selected final protein concentration in the aqueous solution, such that the protein concentration is controllable. Also the type of aqueous solution for dissolving the protein can be selected, as well as the desired pH. For the purpose of the current invention, the previously dried water-soluble insect protein composition provided in step a) of the method of the invention is typically dissolved in water before the provision of the dissolved protein in step a) of the method.

An embodiment is the method according to the invention, wherein after step d) in an optional further step f3) the enzymatically hydrolysed water-soluble insect protein of step d) is concentrated, preferably concentrated such that the dry matter content of the concentrated enzymatically hydrolysed water-soluble insect protein is at least 30% by weight, preferably at least 50% by weight, based on the total weight of the concentrated enzymatically hydrolysed water-soluble insect protein after the concentration step f3). An embodiment is the method of the invention, wherein after the optional method step e2) in an optional further step f4) the Maillard reaction products of enzymatically hydrolysed water-soluble insect protein of step e2) are concentrated, preferably concentrated such that the dry matter content of the concentrated Maillard reaction products of enzymatically hydrolysed water-soluble insect protein of step e2) is at least 30% by weight such as at least 50% by weight based on the total weight of the concentrated Maillard reaction products of enzymatically hydrolysed water-soluble insect protein after the concentration step f4).

An embodiment is the method of the invention, wherein the method comprises the optional concentration step f3), and wherein after said optional concentration step f3) the dry matter content of the concentrated enzymatically hydrolysed water-soluble insect protein is between 30% and 80% by weight based on the total weight of the concentrated enzymatically hydrolysed water-soluble insect protein, preferably between 45% and 75%, more preferably between 50% and 70%. An embodiment is the method of the invention, wherein the method comprises the optional concentration step f4), and wherein after said optional concentration step f4) the dry matter content of concentrated Maillard reaction products of enzymatically hydrolysed water-soluble insect protein is between 30% and 80%, preferably between 45% and 75%, more preferably between 60% and 70% by weight based on the total weight of the concentrated Maillard reaction products of enzymatically hydrolysed water-soluble insect protein.

An embodiment is the method according to the invention, wherein the amount of water-soluble insect protein in the protein/peptidase mixture of step b) is between 0,2% and 30% by weight based on the total weight of the protein/enzyme mixture, preferably 0,5%-25%, more preferably 1%-20%, more preferably 2%-15%, most preferably 3%-10%, such as between 3,5% and 7% by weight based on the total weight of the protein/enzyme mixture, or 3%-5%.

According to embodiments of the invention, either the aqueous water-soluble insect protein composition provided in step a) of the method of the invention, is a concentrated protein composition, or the hydrolysed protein composition provided with the method of the invention is optionally concentrated before use of the hydrolysed protein in for example preparation of pet food, human food stuff, livestock feed, etc., or both. The benefit of providing concentrated aqueous water-soluble insect protein in step a) of the method of the invention relates to controllable speed and extent of protein hydrolysis. That is to say, the enzymatic hydrolysis can occur within a shorter time frame when a more concentrated protein composition is subjected to protein hydrolysis. In addition, the provision of a more concentrated hydrolysed protein composition provides more flexibility when the application of the hydrolysate as a food or feed ingredient is considered. When a concentrated hydrolysed protein composition is subjected to the method of the invention, a smaller volume of the hydrolysed insect protein composition has to be applied during manufacturing of a food product or feed product. This widens the opportunities and applications for use of the water-soluble insect protein hydrolysate and the use of the Maillard reaction products of enzymatically hydrolysed water-soluble insect protein. By applying concentrated aqueous water-soluble insect protein compositions in the method of the invention, dilution of a composition of food or feed ingredients by addition of the product obtained with the method of the invention, is limited. The same for providing concentrated hydrolysed protein with the method of the invention, wherein the hydrolysed protein, or the Maillard reaction products of hydrolysed protein, are subjected to a concentration step, for example before the hydrolysed protein is applied in the manufacture of food stuff for human use, as a food ingredient, a pet food ingredient, an animal feed ingredient, a flavour, a palatant.

An embodiment is the method of the invention, wherein in method step a) the aqueous water-soluble insect protein composition is any one of an aqueous water-soluble insect protein composition derived from house fly, black soldier fly, locust, grasshopper, and cricket. An embodiment is the method of the invention, wherein in step a) the aqueous water-soluble insect protein composition is an aqueous water-soluble insect protein composition derived from any one or more of larvae of beetles, house fly, black soldier fly, locust, grasshopper, cricket, cockroach larvae, palm weevil larvae, silk worm, giant water bug, cicada, bamboo worm, an ant, bush cricket, butterfly, leafhopper, planthopper and bee larvae, and the aqueous water-soluble insect protein composition is preferably derived from black soldier fly, and preferably the aqueous water-soluble insect protein composition is an aqueous water-soluble protein composition derived from black soldier fly larvae. It is preferred that the aqueous water-soluble insect protein composition is derived from black soldier fly, and more preferably the aqueous water-soluble insect protein composition is an aqueous water-soluble protein composition derived from black soldier fly larvae. Typically, such black soldier fly larvae are at an age shortly before the transfer from larvae to pre-pupae phase. Typically, the black soldier fly larvae are between 12 days of age and 25 days of age, such as 16-22 days of age. Such larvae are typically cultured or farmed under conditions of constant feed supply, i.e. ab libitum feeding, and a temperature of 29° C.-32° C., such as 30,5° C.-31° C. The larvae of black soldier fly typically have a protein content of over 35% by weight based on the total weight of the larvae (dry matter base), such as over 40%, over 45%, over 50%, over 55%, over 60%, such as 35%-65%, or less than 63%. Such high protein content makes black soldier fly larvae particularly suitable as a source for retrieving water-soluble insect proteins, suitable for subjecting such proteins to the method of the invention. Surprisingly, when applying an aqueous water-soluble black soldier fly larvae protein composition in the method of the invention, a protein hydrolysate and Maillard reaction products of protein hydrolysate are obtained, which have an intense beef-meat like taste and/or flavour and/or palatability, when e.g. consumed as such by human subjects and e.g. when consumed by humans when incorporated as an ingredient in noodles and a vegetarian burger and e.g. when mixed with cat food and when mixed with dog food.

An embodiment is the method according to the invention, wherein in method step a) the aqueous water-soluble insect protein composition is a water-soluble insect protein composition dissolved in aqueous solution such as water, preferably a water-soluble insect protein composition derived from black soldier fly larvae, wherein the aqueous water-soluble insect protein composition is provided by converting insects into at least an aqueous water-soluble insect protein composition by the steps of, or by at least the steps of:
  (i) providing insects, preferably black soldier fly larvae,
  (ii) reducing the insects of step (i) in size, preferably by mincing, then
  (iii) obtaining a pulp from the insects with reduced size of step (ii), then
  (iv) heating the pulp of step (iii) to a temperature of 70-100° C., then
  (v) subjecting the heated pulp of step (iv) to a physical separation step, preferably encompassing decanting and/or centrifugation, thereby providing the insect protein composition, and then
  (vi) mixing the insect protein composition of step (v) in an aqueous solution such as water or an aqueous buffer, preferably water, therewith providing the aqueous water-soluble insect protein composition of step a).

An embodiment is the method according to the invention, wherein in step a) the aqueous water-soluble insect protein composition is a water-soluble insect protein composition derived from black soldier fly larvae and dissolved in water, wherein the aqueous water-soluble insect protein composition is provided by converting the black soldier fly larvae into at least an aqueous water-soluble insect protein composition by the steps of, or by at least the steps of, preferably by the steps of:
  (i) providing black soldier fly larvae, preferably black soldier fly larvae 12-30 days of age, preferably 14-28 days, more preferably 14-26 days, most preferably 12 hours-3 days before the larvae transform into prepupae, such as 1-2 days before transformation,
  (ii) reducing the black soldier fly larvae of step (i) in size, preferably by mincing, wherein the average particle size of the remains of the insects in the pulp of step a) ranges between 10 micron and 500 micron, then
  (iii) obtaining a pulp from the insects with reduced size of step (ii), then
  (iv) heating the pulp of step (iii) to a temperature of 80-95° C., preferably to a temperature of 85-92° C., heating preferably for a time period of 70 seconds-100 seconds, more preferably 75 seconds-90 seconds, then
  (v) subjecting the heated pulp of step (iv) to a physical separation step, preferably encompassing decanting and/or centrifugation, thereby providing the insect protein composition, and then
  (vi) mixing the insect protein composition of step (v) in water or an aqueous buffer, preferably water, therewith providing the aqueous water-soluble insect protein composition of step a).

Typically, the aqueous water-soluble insect protein composition is derived from black soldier fly larvae as the protein source. It is suitable if the black soldier fly larvae are between 12 and 30 days of age, preferably between 14 and 28 days, more preferably 1426 days, most preferably 12 hours-3 days before the larvae transform into prepupae, such as 1-2 days before transformation, when the black soldier fly larvae are subjected to a protein extraction means and method, for enabling the provision of the aqueous water-soluble insect protein composition of step a) of the method of the invention.

According to the invention, for example minced black soldier fly larvae meat is applied as a source of a water-soluble insect protein composition, provided in an aqueous solution. It is beneficial when the average particle size of the remains of the minced insects range between 10 and 500 micron. The aqueous water-soluble insect protein composition is for example a water-soluble insect protein composition obtained from black soldier fly larvae by applying the method for isolating a proteinaceous fraction from black soldier fly larvae as described in European patent application EP2953487, in the Examples section thereof, in particular Example 1, page 12, line 8-13 and page 13, line 3-5. In some embodiments, the enzymatically hydrolysed water-soluble insect protein provided by the method of the invention is subjected to a Maillard reaction by heating the protein hydrolysate in the presence of added carbohydrate. However, it is preferred when the aqueous water-soluble insect protein composition that is provided in step a) of the method of the invention is a water-soluble insect protein composition obtained from black soldier fly larvae by applying the following larvae processing method steps (i)-(vi) for isolating a proteinaceous fraction from black soldier fly larvae:
  (i) providing black soldier fly larvae, preferably black soldier fly larvae 12-30 days of age, preferably 14-28 days, more preferably 14-26 days, most preferably 12 hours-3 days before the larvae transform into prepupae, such as 1-2 days before transformation,
  (ii) reducing the black soldier fly larvae of step (i) in size, preferably by mincing, wherein the average particle size of the remains of the insects in the pulp of step a) ranges between 10 micron and 500 micron, then
  (iii) obtaining a pulp from the insects with reduced size of step (ii), then
  (iv) heating the pulp of step (iii) to a temperature of 80-95° C., preferably to a temperature of 85-92° C., heating preferably for a time period of 70 seconds-100 seconds, more preferably 75 seconds-90 seconds, then (v) subjecting the heated pulp of step (iv) to a physical separation step, preferably encompassing decanting and/or centrifugation, thereby providing the insect protein composition, and then (vi) mixing the insect protein composition of step (v) in water or an aqueous buffer, preferably water, therewith providing the aqueous water-soluble insect protein composition of step a) of the method for producing an enzymatically hydrolysed water-soluble insect protein according to the invention.

The inventors established that by applying this larvae processing method steps as part of the method of the invention, in step a) of the method, a protein pulp obtained from black soldier fly larvae as the protein source, is obtained which pulp has surprisingly improved features and structural characteristics, when compared to pulp obtained from such larvae by applying an alternative black soldier fly larvae processing method known in the art, such as the method outlined in European patent application EP2953487, in the Examples section thereof, in particular Example 1, page 12, line 8-13 and page 13, line 3-5. In particular, the relatively short heating time of less than 100 seconds, in step (iv) of the method of the invention, is deemed essential for obtaining improved larvae pulp. It has been found by the inventors that by using the time-temperature combination less oil is entrapped within the protein fraction, therewith providing a more pure protein source in step a) of the method of the invention, compared with protein sources provided using alternative, current means and methods for isolating protein pulp from black soldier fly larvae as the protein source. It has also been found that discolouration of the pulp (of protein) due to Maillard reactions is largely avoided, thereby improving the quality of the product obtained. For example, protein with reduced fat content is obtained when minced black soldier fly larvae are heated for 80 seconds at 90° C., or for 75-85 seconds at a temperature of 90° C.±2° C. In EP2953487, heating time is at least 5 minutes and even 30 minutes. Furthermore, the relatively short heating time of at most 100 seconds, preferably about 70-90 seconds, of the minced black soldier fly pulp results in less granulated and less aggregated insect pulp compared to longer heating times applied in current methods known in the art. Less granulated larvae pulp is beneficial for the enzymatic hydrolysis of the protein comprised by the pulp. Granulation reduces enzyme efficiency since the particulate matter is less accessible for the enzyme molecules. By applying the larvae processing method steps as part of the method of the invention, the short heating time results in a protein composition consisting of smaller protein clusters, aggregates, particles, or even (mainly) of protein monomers and/or small multimers, compared with the larger protein aggregates and particles obtained when black soldier fly larvae pulp is subjected to heating for over 100 seconds such as for 5 minutes up to 30 minutes.

It is preferred that the black soldier fly subjected to the method of the invention, are black soldier fly larvae. A typical method for converting insects such as black soldier fly larvae into an aqueous water-soluble insect protein composition suitable for application in the method of the invention for producing an enzymatically hydrolysed water-soluble insect protein, is provided in European patent application EP2953487, in the Examples section thereof, in particular Example 1, page 12, line 8-13 and page 13, line 3-5. The heating step (iv) typically lasts for between 50 seconds and 120 seconds, preferably for 80 seconds, and typically the heating temperature in step (iv) is 80° C.-95° C. and preferably about 90° C. According to the method of the invention, a high protein yield is achievable when the insect pulp is in step (iv) heated for 80 seconds at 90° C., when black soldier fly larvae are provided in step (i). In some embodiments, the enzymatically hydrolysed water-soluble insect protein provided by the method of the invention is subjected to a Maillard reaction by heating the protein hydrolysate in the presence of added carbohydrate. In some embodiments, the source of water-soluble insect proteins is for example also an aqueous water-soluble insect protein composition provided with the method described in EP2953487, in the Examples section thereof, in particular Example 1, page 12, line 8-13 and page 13, line 3-5, that is subjected to the method steps a)-d) of the method of the invention, before being further subjected to the method steps e1) and e2) according to the invention, therewith providing Maillard reaction products and/or advanced glycation endproducts. See also FIG. 1 for an outline of the steps for the provision of an aqueous water-soluble insect protein composition and for the provision of hydrolysed protein and Maillard reaction products of hydrolysed protein, according to the method of the invention.

An embodiment is the method according to the invention, wherein the enzymatically hydrolysed water-soluble insect protein provided in method step d) is soluble in an aqueous solution such as water or a buffered aqueous solution to an extent of at least 60% by weight based on the weight of the total amount of the enzymatically hydrolysed water-soluble insect protein provided in step d), preferably at least 70%, such as 70%-100%. An embodiment is the method according to the invention, wherein the Maillard reaction products of enzymatically hydrolysed water-soluble insect protein provided in step e2) of the method is soluble in an aqueous solution such as water or a buffered aqueous solution to an extent of at least 60% by weight based on the weight of the total amount of the Maillard reaction products of enzymatically hydrolysed water-soluble insect protein provided in step e2) of the method, preferably at least 70%, such as 70%-100%. When protein derived from black soldier fly larvae is considered, the protein solubility in an aqueous solution such as water at pH 7, is at least 90% and is essentially 100% by weight based on the total amount of protein present in the protein obtained from black soldier fly larvae according to the steps (i)-(v) as here above outlined.

An aspect of the invention relates to an enzymatically hydrolysed water-soluble insect protein obtained by the method for producing an enzymatically hydrolysed water-soluble insect protein of the invention, or obtainable by the method for producing an enzymatically hydrolysed water-soluble insect protein of the invention. A further aspect of the invention relates to Maillard reaction products of enzymatically hydrolysed water-soluble insect protein obtained by the method for producing an enzymatically hydrolysed water-soluble insect protein of the invention including further steps for the provision of Maillard reaction products, or obtainable by the method for producing an enzymatically hydrolysed water-soluble insect protein of the invention including further steps for the provision of Maillard reaction products.

An embodiment is the enzymatically hydrolysed water-soluble insect protein obtained by the method for producing an enzymatically hydrolysed water-soluble insect protein of the invention, or obtainable by the method for producing an enzymatically hydrolysed water-soluble insect protein of the invention or the Maillard reaction products of enzymatically hydrolysed water-soluble insect protein obtained by the method for producing an enzymatically hydrolysed water-soluble insect protein of the invention including further steps for the provision of Maillard reaction products, or obtainable by the method for producing an enzymatically hydrolysed water-soluble insect protein of the invention including further steps for the provision of Maillard reaction products, wherein the insect protein source is black soldier fly larvae protein according to embodiments of the invention and/or wherein the insect protein source is provided according to the steps (i)-(vi) of the larvae processing method of the invention.

An aspect of the invention relates to an enzymatically hydrolysed water-soluble insect protein or relates to Maillard reaction products of enzymatically hydrolysed water-soluble insect protein, wherein at least 50% by weight of said protein has a molecular weight of less than 1,000 Dalton, based on the total weight of said protein, preferably 55%-100%, more preferably 65%-100%, most preferably 75%-100%, such as 80%-95% or 85%-90% or 85%-100%. The insect protein is preferably water-soluble black soldier fly larvae protein, such as an aqueous water-soluble black solider fly larvae protein composition. Such a protein composition derived from larvae such as black soldier fly larvae is preferably obtained by applying the method as described in European patent application EP2953487, in the Examples section, Example 1, page 12, line 8-13 and page 13, line 3-5.

An embodiment is the enzymatically hydrolysed water-soluble insect protein according to the invention, wherein at least 10% by weight of the protein is free amino-acid residues, based on the total weight of said protein, preferably 15%-60%, more preferably 20%-55%, most preferably 35%-50%, such as 25%-40% or 45%-55%. An embodiment is the Maillard reaction products of enzymatically hydrolysed water-soluble insect protein according to the invention, wherein at least 10% by weight of the protein is free amino-acid residues, based on the total weight of said protein, preferably 15%-60%, more preferably 20%-50%, most preferably 25%-35%, such as 25%-40% or 35%-50%. Typically, subjecting a water-soluble insect protein composition to the method of the invention results in an enzymatically hydrolysed insect protein composition comprising 33%-48% by weight free amino-acid residues based on the total weight of the proteins in the protein composition. Subjecting the enzymatically hydrolysed insect proteins to the optional method steps e1) and e2) of the Maillard reaction, according to the invention, results in typically 33%-48% by weight free amino-acid residues based on the total weight of the proteins in the protein composition, wherein a fraction of said free amino-acid residues is now provided as Maillard reaction products, such as Arg residues. An embodiment is the enzymatically hydrolysed water-soluble insect protein or Maillard reaction products of enzymatically hydrolysed water-soluble insect protein according to the invention, wherein at least 10% by weight of the protein is free amino-acid residues, based on the total weight of said protein, preferably 15%-60%, more preferably 20%-55%, most preferably 30%-50%, such as 25%-40% or 35%-50%.

An embodiment is the enzymatically hydrolysed water-soluble insect protein of the invention, wherein at least 2,5% by weight is free arginine, and/or at least 2,5% by weight is free glutamic acid, and/or at least 1,25% by weight is free leucine, and/or at least 2,2% by weight is free lysine, based on the total weight of said enzymatically hydrolysed water-soluble insect protein, preferably, at least 3,7% by weight is free arginine, at least 3,0% by weight is free glutamic acid, at least 1,5% by weight is free leucine, and at least 2,6% by weight is free lysine, based on the total weight of said enzymatically hydrolysed water-soluble insect protein, and preferably, less than 4,7% by weight is free arginine, and/or less than 4,0% by weight is free glutamic acid, and/or less than 3,0% by weight is free leucine, and/or less than 4,0% by weight is free lysine, based on the total weight of said enzymatically hydrolysed water-soluble insect protein, preferably less than 4,5% by weight is free arginine, and less than 3,7% by weight is free glutamic acid, and less than 2,7% by weight is free leucine, and less than 3,6% by weight is free lysine, based on the total weight of said enzymatically hydrolysed water-soluble insect protein.

An embodiment is the Maillard reaction products of enzymatically hydrolysed water-soluble insect protein of the invention, wherein at least 2,5% by weight is free arginine, and/or at least 2,5% by weight is free glutamic acid, and/or at least 1,25% by weight is free leucine, and/or at least 2,2% by weight is free lysine, based on the total weight of said Maillard reaction products of enzymatically hydrolysed water-soluble insect protein, preferably, at least 3,7% by weight is free arginine, at least 3,0% by weight is free glutamic acid, at least 1,5% by weight is free leucine, and at least 2,6% by weight is free lysine, based on the total weight of said Maillard reaction products of enzymatically hydrolysed water-soluble insect protein, and preferably, less than 4,7% by weight is free arginine, and/or less than 4,0% by weight is free glutamic acid, and/or less than 3,0% by weight is free leucine, and/or less than 4,0% by weight is free lysine, based on the total weight of said Maillard reaction products of enzymatically hydrolysed water-soluble insect protein, preferably less than 4,5% by weight is free arginine, and less than 3,7% by weight is free glutamic acid, and less than 2,7% by weight is free leucine, and less than 3,6% by weight is free lysine, based on the total weight of said Maillard reaction products of enzymatically hydrolysed water-soluble insect protein.

An embodiment is the enzymatically hydrolysed water-soluble insect protein of the invention, wherein said water-soluble protein comprises a microbial count in cfu/g protein of less than 50 such as 10 or less than 10 for *E. coli*, and/or less than 1 such as 0 for *Salmonella*, and/or less than 500 such as less than 150 or less than 10 for *B. cereus*, and/or less than 500 such as less than 50 and preferably less than 10 for *C. perfringens*, preferably the microbial count in cfu/g protein is less than 10 for *E. coli*, and/or less than 0,1 for *Salmonella* and preferably *Salmonella* is absent, and/or less than 10 for *B. cereus*, and/or less than 10 for *C. perfringens*, more preferably said water-soluble protein comprises a microbial count in cfu/g protein of less than 10 for *E. coli*, less than 10 for *B. cereus*, and less than 10 for *C. perfringens*, wherein the microbial count is 0 cfu/g protein for *Salmonella* when the *Salmonella* count in 25 gram of the enzymatically hydrolysed water-soluble insect protein is determined (*Salmonella* is not detectable in a sample of 25 gram of the enzymatically hydrolysed water-soluble insect protein).

An embodiment is the Maillard reaction products of enzymatically hydrolysed water-soluble insect protein of the invention, wherein said water-soluble protein comprises a microbial count in cfu/g protein of less than 50 such as 10 or less than 10 for *E. coli*, and/or less than 1 such as 0 for *Salmonella*, and/or less than 500 such as less than 150 or less than 10 for *B. cereus*, and/or less than 500 such as less than 50 and preferably less than 10 for *C. perfringens*, preferably the microbial count in cfu/g protein is less than 10 for *E. coli*, and/or less than 0,1 for *Salmonella* and preferably *Salmonella* is absent, and/or less than 10 for *B. cereus*, and/or less than 10 for *C. perfringens*, more preferably said water-soluble protein comprises a microbial count in cfu/g protein of less than 10 for *E. coli*, less than 10 for *B. cereus*, and less than 10 for *C. perfringens*, wherein the microbial count is 0 cfu/g protein for *Salmonella* when the *Salmonella* count in 25 gram of the enzymatically hydrolysed water-soluble insect protein is determined (*Salmonella* is not detectable in a sample of gram of the enzymatically hydrolysed water-soluble insect protein).

Both the enzymatically hydrolysed water-soluble insect protein of the invention and the Maillard reaction products of enzymatically hydrolysed water-soluble insect protein of the invention have a microbial count expressed in cfu/g protein that is below the upper limit for the indicated microbes that is allowed by the European Commission, when the application of the hydrolysed protein as a food product or a food ingredient for human use is considered. See also FIG. 2.

An embodiment is the enzymatically hydrolysed water-soluble insect protein of the invention, wherein the water-soluble protein is provided with the method according to the invention. An embodiment is the Maillard reaction products of enzymatically hydrolysed water-soluble insect protein of the invention, wherein the water-soluble protein is provided with the method according to the invention. An embodiment is the enzymatically hydrolysed water-soluble insect protein of the invention or the Maillard reaction products of enzymatically hydrolysed water-soluble insect protein of the invention, wherein the insect protein source is black soldier fly larvae protein. In particular, the protein source is provided in step a) of the method of the invention by applying the steps (i)-(vi) of the black soldier fly larvae processing method of the invention.

An embodiment is the enzymatically hydrolysed water-soluble insect protein of the invention, further comprising any one or more of a palatability enhancer and a humectant, or any combination thereof. An embodiment is the Maillard reaction products of enzymatically hydrolysed water-soluble insect protein of the invention, further comprising any one or more of a palatability enhancer and a humectant, or any combination thereof.

An embodiment is the enzymatically hydrolysed water-soluble insect protein of the invention, wherein the palatability enhancer is a metal pyrophosphate, 2-methyl furan, 2-methyl pyrrole, dimethyl disulfide and/or wherein the humectant is selected from propylene glycol, glycerine, corn syrup and a mineral salt. An embodiment is the Maillard reaction products of enzymatically hydrolysed water-soluble insect protein of the invention, wherein the palatability enhancer is a metal pyrophosphate, 2-methyl furan, 2-methyl pyrrole, dimethyl disulfide and/or wherein the humectant is selected from propylene glycol, glycerine, corn syrup and a mineral salt.

An aspect of the invention relates to the use of the enzymatically hydrolysed water-soluble insect protein of the invention in the production of a pet food product, a pet food ingredient, an animal feed product or animal feed ingredient, or in the production of a human food product or human food ingredient, preferably in the production of a cat feed, a dog feed or a shrimp feed such as feed for white leg shrimp. A further aspect of the invention relates to the Maillard reaction products of enzymatically hydrolysed water-soluble insect protein of the invention in the production of a pet food product, a pet food ingredient, an animal feed product or animal feed ingredient, or in the production of a human food product or human food ingredient, preferably in the production of a cat feed, a dog feed or a shrimp feed such as feed for white leg shrimp. An embodiment is the aforementioned use, wherein the pet is a dog or a cat, preferably a dog, or wherein the animal is a dog, a cat or a shrimp, preferably white leg shrimp (*Litopenaeus vannamel*).

An embodiment is the use according to the invention, wherein the produced pet food product, pet food ingredient, animal feed product or animal feed ingredient is any of a food or a food ingredient or a feed or a feed ingredient for pet, cat, dog, fish, shrimp such as white leg shrimp, tuna, cod, a farmed marine organism, a farmed fresh water organism, turbot, salmon, carp, a weaning animal, a post weaning animal, preferably for cat, dog, shrimp such as white leg shrimp, or is a feed or food flavour or a feed or food flavour enhancer, or wherein the produced human food product or the produced human food ingredient is any of a broth, a sauce, a flavour, a food flavour, a food flavour enhancer, a soup, a meat substitute product or ingredient or a meat replacement product or ingredient such as a substitute for boiled beef, beef broth, pork broth, beef meat, cooked meat.

An embodiment is the use according to the invention, wherein the produced pet food product, pet food ingredient, animal feed product or animal feed ingredient is any of a food or a food ingredient or a feed or a feed ingredient for pet, cat, dog, fish, shrimp, tuna, cod, a farmed marine organism, a farmed fresh water organism, turbot, salmon, carp, a weaning animal, a post weaning animal, a feed for an insect species different from the insect species applied in the method of the invention and different from the insect species from which the enzymatically hydrolysed water-soluble insect protein of the invention were obtained and derived or the Maillard reaction products of enzymatically hydrolysed water-soluble insect protein according to the invention were obtained and derived, such as for example a pollinator such as, but not limited to a bee or a beneficial used in biocontrol, for example, but not limited to lady bug, and such as bumblebee, mosquito, termite and fruitfly; or is a feed or food flavour or a feed or food flavour enhancer, or wherein the produced human food product or the produced human food ingredient is any of a broth, a sauce, a flavour, a food flavour, a food flavour enhancer, a soup, a meat substitute product or ingredient or a meat replacement product or ingredient such as a substitute for boiled beef, beef broth, pork broth, beef meat, cooked meat. Typically, the enzymatically hydrolysed water-soluble insect protein of the invention or the Maillard reaction products of enzymatically hydrolysed water-soluble insect protein according to the invention is obtained and derived from BSF larvae. For the feed for an insect species different from the insect species applied in the method of the invention and different from the insect species from which the enzymatically hydrolysed water-soluble insect protein of the invention were obtained and derived or the Maillard reaction products of enzymatically hydrolysed water-soluble insect protein according to the invention were obtained and derived, such an insect species is thus typically different from larvae of beetles, house fly, black soldier fly, locust, grasshopper, cricket, cockroach larvae, palm weevil larvae, silk worm, giant water bug, cicada, bamboo worm, an ant, bush cricket, butterfly, leafhopper, planthopper and bee larvae, preferably different from house fly, black soldier fly, locust, grasshopper, cricket, cockroach larvae, palm weevil larvae, silk worm, giant water bug, cicada, bamboo worm, an ant, bush cricket, butterfly, leafhopper, planthopper and bee larvae, and preferably different from BSF, in particular BSF larvae.

An aspect of the invention relates to an animal feed product or an animal feed ingredient or a pet food product or a pet food ingredient comprising, or consisting of, the enzymatically hydrolysed water-soluble insect protein or the Maillard reaction products of enzymatically hydrolysed water-soluble insect protein of the invention, preferably a cat feed product or ingredient, a dog feed product or ingredient or a shrimp feed product or ingredient such as a feed product or ingredient for white leg shrimp, or a human food product or a human food ingredient comprising, or consisting of, the enzymatically hydrolysed water-soluble insect protein or the Maillard reaction products of enzymatically hydrolysed water-soluble insect protein of the invention.

An embodiment is the pet food product, pet food ingredient, animal feed product or animal feed ingredient according to the invention, wherein the pet food product, pet food ingredient, animal feed product or animal feed ingredient is any of a food or a feed or a food ingredient or a feed ingredient for pet, cat, dog, fish, shrimp, tuna, cod, a farmed marine organism, a farmed fresh water organism, turbot, salmon, carp, a weaning animal, a post weaning animal, preferably a cat, dog or shrimp such as white leg shrimp, or is a food flavour or a food flavour enhancer or a feed flavour or a feed flavour enhancer, or the human food product or the human food ingredient according to the invention, wherein the human food product or the human food ingredient is any of a broth, a sauce, a burger, a hamburger, a noodle, a flavour, a food flavour or a food flavour enhancer, a soup, a meat substitute product or ingredient or a meat replacement product or ingredient such as a substitute for boiled beef, beef broth, pork broth, beef meat, cooked meat, beef-meat based hamburger, beef-meat based burger, beef-meat based soup, noodles, etc., etc.

A sixth aspect of the invention relates to use of the enzymatically hydrolysed water-soluble insect protein or the Maillard reaction products of enzymatically hydrolysed water-soluble insect protein of the invention as an antioxidant. In particular, as a food or feed ingredient with antioxidant activity. The enzymatically hydrolysed water-soluble insect protein and the Maillard reaction products of enzymatically hydrolysed water-soluble insect protein of the invention thus have antioxidant properties.

A seventh aspect of the invention relates to use of the animal feed product or the animal feed ingredient or the pet food product or the pet food ingredient of the invention as an antioxidant and/or as an ingredient with health promoting potential.

An aspect of the invention relates to the animal feed product or the animal feed ingredient or the pet food product or the pet food ingredient of the invention for use in a method for the prevention and/or suppression of cellular oxidative damage.

A further aspect of the invention relates to an animal feed product or an animal feed ingredient or a pet food product or a pet food ingredient comprising the enzymatically hydrolysed water-soluble insect protein or the Maillard reaction products of enzymatically hydrolysed water-soluble insect protein of the invention with antioxidant activity according to the invention. The antioxidant activity of the animal feed product or the animal feed ingredient or the pet food product or the pet food ingredient comprising the enzymatically hydrolysed water-soluble insect protein or the Maillard reaction products of enzymatically hydrolysed water-soluble insect protein is due to the antioxidant properties of the enzymatically hydrolysed water-soluble insect protein or the Maillard reaction products of enzymatically hydrolysed water-soluble insect protein of the invention.

The inventors surprisingly established and analyzed in vitro antioxidant activity of black soldier fly aqueous protein hydrolysates obtained from BSF larvae, wherein the antioxidant activity of Black soldier fly—aqueous protein hydrolysate (BSF-APH) was analyzed using radical scavenging models (DPPH and ABTS assays), enzymatic models involving myeloperoxidases response (classical and SIEFED assays), and a cellular model involving neutrophil response (See the Examples section, here below). Commercial fish meal and chicken meal were used as industrial benchmarks in the comparative examples. In comparative examples, outcomes of tests revealed that fish meal and chicken meal offer little to no advantage in terms of suppressing the oxidative damage occurring as a result of neutrophil and myeloperoxidase response. Moreover, fish meal and chicken meal also exhibit pro-oxidant behavior in some of the models used in this study. Results surprisingly show that black soldier fly aqueous protein hydrolysate is effective in protecting against the cellular (oxidative) damage resulting from host neutrophil and myeloperoxidase response. Therefore, black soldier fly aqueous protein hydrolysate (APH) of the invention shows advantages over chicken meal and fish meal for inclusion as an ingredient in pet food and aquaculture feed formulations, for example as a food or feed ingredient.

The inventors established that BSF aqueous proteins hydrolysates have a significant share of proteins <1000 Da. This includes a mixture of short chain peptides and free amino acids. Some short chain peptides and free amino acids are known to possess anti-oxidant activity. These molecules can actively scavenge ROS and free radicals. Firmansyah and Abduh [3] evaluated the DPPH (2,2-diphenyl-1-picrylhydrazyl) scavenging activity of BSF protein hydrolysates. Zhu et al. [4] evaluated the DPPH, ABTS (2,2'-azino-bis(3-ethylbenzothiazoline-6-sulfonic acid), superoxide and hydroxyl radical scavenging activity of BSF protein hydrolysates. No studies have been realized till date, to the best of the knowledge of the inventors, that established the antioxidant activity of BSF protein hydrolysate using fundamental enzymatic and cellular models, showing the surprisingly high anti-oxidant activity and surprisingly high protection against oxidative stress and/or damage by the hydrolysed BSF larvae protein (BSF-APH). Therefore, before the currently established invention, the antioxidant potential of BSF protein hydrolysates is poorly understood on a fundamental level and was not yet disclosed, nor anticipated, nor expected. According to the invention, detailed investigations on the in vitro antioxidant activity of BSF protein hydrolysates unlock new applications of these protein derivatives to improve animal health.

The inventors unraveled the surprisingly high antioxidant potential and activity of BSF protein hydrolysates, using: (1) radical scavenging models involving DPPH and ABTS; (2) enzymatic models involving myeloperoxidases response; and (2). a cellular model involving neutrophil response. Chicken meal and fish meal were used as industrial benchmarks in comparative examples for comparison with the anti-oxidant activities of the BSF protein hydrolysates according to the invention.

An aspect of the invention relates to the animal feed product or the animal feed ingredient or the pet food product or the pet food ingredient of the invention for use in a method for the prevention and/or suppression of a pro-inflammatory response induced by reactive oxygen species.

An aspect of the invention relates to the use of the animal feed product or the animal feed ingredient or the pet food product or the pet food ingredient of the invention with anti-oxidant potential.

The term 'anti-oxidant property' has its regular scientific meaning and here refers to a compound or a composition, such as the hydrolysed protein of the invention, that consists of or comprises an antioxidant with antioxidant activity, such as an anti-inflammatory response. Typically, such an anti-inflammatory response is a response to the inflammatory response induced by for example reactive oxygen species, e.g. in the cells of a mammal such as a pet or a human subject, or in the cells of a fish. Reference is made to for example book chapters 1, 5 and 6 of "Antioxidants in Food: Practical Applications" (Jan Pokorny, Nedyalka Yanishlieva and Michael Gordon (editors), 2001, Cambridge: CRC Press, Woodhead Publishing Ltd. ISBN 1 85573 463 X, CRC Press, ISBN 0-8493-1221-1). An anti-oxidant is a compound with anti-oxidant activity or a composition with anti-oxidant activity or a composition comprising a compound with anti-oxidant activity, such as activity against the oxidative damage resulting from host immune response. An anti-oxidant for example inhibits oxidation. Oxidation, e.g. reactive oxygen species, in a subject for example induces cellular (oxidative) damage.

The term 'health promoting', such as in 'health promoting food', 'health promoting activity', 'health promoting property', and 'health promoting potential', has its regular scientific meaning and here refers to the effect of a compound or a composition, such as the hydrolysed protein of the invention, on the health of an animal such as a mammal such as a pet animal or a human subject, when such compound or composition is consumed by the animal. Consumption of the compound or composition with health promoting potential contributes to or supports or promotes or increases or maintains the health status of the animal such as a mammal such as a pet animal or a human subject. Reference is made to for example book chapters 1, 5 and 6 of "Antioxidants in Food: Practical Applications" (Jan Pokorny, Nedyalka Yanishlieva and Michael Gordon (editors), 2001, Cambridge: CRC Press, Woodhead Publishing Ltd. ISBN 1 85573 463 X, CRC Press, ISBN 0-8493-1221-1).

The present invention has been described above with reference to a number of exemplary embodiments. Modifications are possible, and are included in the scope of protection as defined in the appended claims. The invention is further illustrated by the following examples, which should not be interpreted as limiting the present invention in any way.

EXAMPLES

Example 1

An aqueous water-soluble protein composition or a dried water-soluble protein composition wherein the water-soluble proteins are substantially completely dissolvable in an aqueous solution such as water, is provided by isolating a proteinaceous fraction from black soldier fly larvae according to the method as described in European patent application EP2953487, in the Examples section, Example 1, page 12, line 8-13 and page 13, line 3-5. In brief, larvae of black soldier fly were provided and subjected to the method to convert insects or worms into nutrient streams, as substantially outlined here below (See also FIG. 1):

Method to convert insects or worms into nutrient streams, comprising the steps of:
  (a1) providing insects or worms, here larvae of black soldier fly
  (a2) reducing the insects or worms in size,
  (a3) obtaining a pulp from insects or worms, then
  (b) heating the pulp to a temperature of 70-100° C., and then
  (c) subjecting the heated pulp to a physical separation step thereby obtaining a fat fraction, an aqueous protein fraction (referred to as "larvae water") and a solid-containing fraction.

The aqueous protein fraction is an aqueous water-soluble protein fraction when black soldier fly larvae are subjected to the method to convert insects into nutrient streams. The aqueous water-soluble protein fraction is in some embodiments dried after step (c) using spray-drying, therewith providing dried black soldier fly larvae proteins. The method does not comprise enzymatic treatment of the pulp in any of the steps of the method. Optionally, the method does comprise enzymatic treatment of the larvae pulp, though for the current example, no enzymatic digestion steps were applied in the method to convert black soldier fly larvae into nutrient streams. In step (b) of the method, the minced black soldier fly larvae are pasteurized by heating the pulp (or 'puree') at 90° C. for 80 seconds, therewith providing pasteurized 'meat' of larvae. The pasteurized meat is subsequently in step (c) mechanically separated to obtain the liquid protein fraction (larvae water). The aqueous protein fraction is either used directly 'as is' without further treatment steps (for example drying or concentration) before provided as aqueous insect- or worm protein composition comprising at least one protein in step (a) of the method of the invention for the provision of enzymatically hydrolysed insect- or worm proteins and for the provision of Maillard reaction products of enzymatically hydrolysed insect- or worm proteins, or the aqueous protein fraction (larvae water) is first concentrated, for example three to twelve times, such as 5-10 times, or first dried for example using spray-drying, before being subjected to dissolving in an aqueous solution such as water, and then provided in step (a) of the method of the invention as aqueous insect- or worm protein composition comprising at least one protein.

The crude protein content of the larvae water obtained with step (c) of the here above outlined method to convert insects or worms into nutrient streams, was 3,8% by weight based on the total weight of the larvae water. The crude fat content was 0,3% by weight based on the total weight of the larvae water. For the obtained larvae water, the total plate count assessed as the aerobic mesophilic count at 30° C. (ISO 4833) was 26000 cfu/g; the *Bacillus cereus* count at 30° C. (ISO 7932) was <40 cfu/g; the *Clostridium perfringens* count at 37° C. (ISO 7937) was <10 cfu/g; the *Escherichia coli* count at 44° C. was <10 cfu/g; and *Salmonella* was not detected in 25 g of the product, using PCR fast method (ISO 6579). Thus, in the larvae water, the microbial count was less than 40 cfu/g protein for *Bacillus cereus*; less than 10 cfu/g protein for *Clostridium perfringens*; less than 10 cfu/g protein for *Escherichia co/i*; and the *Salmonella* count was 0 cfu/g protein when 25 g of the larvae water was assessed. Herewith, the microbial count was within value boundaries that should be reached for application of the larvae water in food products or food ingredients.

The aqueous water-soluble protein fraction (larvae water), either or not concentrated, or first dried and then dissolved again, is applied as the substrate for enzymatic hydrolysis of the at least one protein in black soldier fly larvae water-soluble protein fraction. The liquid aqueous water-soluble protein fraction contains approximately 91% moisture content by weight, about 4% proteins by weight based on the total weight of the aqueous protein fraction (larvae water), and the liquid aqueous protein fraction had low fat content (<1% by weight based on the total weight of the aqueous protein fraction, i.e. 0,3% for the current preparation). The larvae water is a stock solution of dissolved water-soluble proteins that does not need any dilution step before enzymatic hydrolysis of the water-soluble proteins. The aqueous water-soluble protein fraction (larvae water) does not comprise water-insoluble chitin.

Enzymatic Hydrolysis

The aqueous water-soluble protein fraction (larvae water) was subjected to enzymatic hydrolysis in a bioreactor with temperature control (30° C. to 100° C.), pH control (pH is between 4 and 9) and with continuous stirring (up to 1250 rpm). The proteins were enzymatically hydrolysed in some examples using a single amino-peptidase and in further examples using a combination of aminopeptidases which have endopeptidase and exopeptidase activities. The enzyme concentration was 0.1% to 2% by weight based on the total weight of the aqueous water-soluble protein fraction comprising the enzyme(s), for the one or more amino-peptidases. For example, Flavourzyme (Novozymes, Denmark) was used at 1% by weight based on the total weight of the aqueous protein fraction comprising the enzyme(s).

Reaction Conditions

During enzymatic hydrolysis, the pH (typically between 4 to 8), the reaction temperature (typically from 35° C. to 60° C.) and the enzymatic hydrolysis time (typically from 2 hours to 12 hours) of the reaction depended on the type of selected enzyme(s). With the Flavourzyme, the aqueous water-soluble protein fraction was hydrolysed at pH 7 (which was also the pH of the larvae water), at a temperature of 50° C. during 6 hours.

Heating to Induce Enzyme Deactivation

The enzymatic hydrolysis reactions were terminated by heat deactivation of enzyme(s) at 75° C. to 110° C. for 1 minute to 10 minutes. Commonly, the enzymatic hydrolysis reaction was terminated by heating the reaction mixture of the aqueous water-soluble protein fraction comprising the enzyme(s), at 100° C. for 2 minutes, providing enzymatically hydrolysed black soldier fly larvae water-soluble proteins. When the Flavourzyme enzymes were applied, the enzymatically hydrolysed proteins are referred to as Hydrolysed Insect Extract 1 ("HIE1", or "HIE 1").

Optional Step

Cooking of the Enzymatically Hydrolysed Proteins to Induce Maillard Reaction

The Maillard reaction is carried out by carefully heating the provided enzymatically hydrolysed insect proteins at 100° C. to 170° C. for 5 minutes to 60 minutes after addition of 0.05% to 1% glucose or sucrose by weight based on the total weight of the enzymatically hydrolysed proteins mixed with the added carbohydrate. The Maillard reaction was for example conducted by heating HIE1 that was mixed with 1% by weight sucrose based on the total weight of HIE1 mixed with sucrose, at 150° C. for 15 minutes. This Maillard reaction provided Maillard reaction products of enzymatically hydrolysed black soldier fly larvae proteins, referred to as Hydrolysed Insect Extract 2 ("HIE2", or "HIE 2").

Final Product

The compositions HIE 1 and HIE 2 are subsequently subjected to experiments for testing flavour, palatability, etc., by either using the solution provided with the method of the invention for providing the enzymatically hydrolysed water-soluble insect protein or for providing the Maillard reaction products of enzymatically hydrolysed water-soluble insect protein, or HIE 1 and/or HIE 2 are first subjected to a concentration step by evaporating the aqueous solution such that the dry matter content is for example at least 30% by weight such as for example at least 50% by weight of the total weight of the concentrated HIE 1 or HIE 2. Alternatively, the HIE 1 or the HIE 2 is applied as dried hydrolysed protein, for example as a powder, by an evaporation step executed with HIE 1 or with HIE 2, and a drying step for example using a fluidized bed dryer and/or using a spray dryer, such that the dry matter (DM) content of the dried HIE 1 or the dried HIE 2 is at least 92% by weight DM based on the total weight of the dried HIE 1 or based on the total weight of the dried HIE 2.

Composition

The chemical compositions of the enzymatically hydrolysed black soldier fly larvae water-soluble proteins HIE 1 and of the Maillard reaction products of enzymatically hydrolysed black soldier fly larvae water-soluble proteins HIE 2 are outlined in Table 1. In addition, the chemical composition of the aqueous water-soluble protein fraction of black soldier fly larvae (larvae water) is provided in Table 1. The free amino acid compositions of the aqueous water-soluble protein fraction of black soldier fly larvae (larvae water) and HIE 1 are outlined in Table 2. While counts of some pathogenic microbes is mentioned in table 3.

TABLE 1

Chemical compositions of the aqueous water-soluble protein fraction of black soldier fly larvae (larvae water), the enzymatically hydrolysed black soldier fly larvae proteins HIE 1 and the Maillard reaction products of enzymatically hydrolysed black soldier fly larvae proteins HIE 2

| Component[‡] | Aqueous water-soluble protein fraction of black soldier fly larvae (larvae water) | HIE 1 | HIE 2 |
|---|---|---|---|
| Moisture | 90.9% | 90.8 | 88.7 |
| Proteins | 3.8% | 3.8% | 4.0% |
| Lipids | 0.3% | <0.3% | 0.3% |
| Ash | 1.2% | 1.3% | 1.3% |
| Starch | 0.8% | <0.5% | <0.5% |
| Total sugars (including glucose) | 0.9% | 1.5% | 1.9% |

[‡]the amounts of the listed components are provided as the weight percentage based on the total weight of the analysed compositions.

TABLE 2

Free amino acid composition of the enzymatically hydrolysed black soldier fly larvae proteins HIE 1. The amounts of the free amino acids is determined by applying the DJA75 test (ISO 13903: 2005/IC-UV).

| Component | HIE 1 | HIE 2 |
|---|---|---|
| Pepsin Digestibility | 100% | 100% |
| Proteins <1000 Da (weight % of total weight of proteins) | 100% | 87.5% |
| Free amino acid content (weight % of total weight of proteins) | 47.7% | 46.3% |
| Free Alanine[‡] | 0.272% | 0.282% |
| Free Arginine | 0.171% | 0.177% |
| Free Aspartic acid | 0.0740% | 0.0790% |

TABLE 2-continued

Free amino acid composition of the enzymatically hydrolysed black soldier fly larvae proteins HIE 1. The amounts of the free amino acids is determined by applying the DJA75 test (ISO 13903: 2005/IC-UV).

| Component | HIE 1 | HIE 2 |
|---|---|---|
| Free Cysteine | 0.0180% | 0.0200% |
| Free Glutamic acid | 0.137% | 0.138% |
| Free Glycine | 0.0860% | 0.0890% |
| Free Histidine | 0.0940% | 0.0970% |
| Free Isoleucine | 0.0620% | 0.0570% |
| Free Leucine | 0.0940% | 0.0860% |
| Free Lysine | 0.116% | 0.119% |
| Free Methionine | 0.0120% | 0.0120% |
| Free Phenylalanine | 0.0560% | 0.0580% |
| Free Proline | 0.172% | 0.179% |
| Free Serine | 0.0700% | 0.0730% |
| Free Threonine | 0.0850% | 0.0860% |
| Free Tryptophane | 0.0360% | 0.0380% |
| Free Tyrosine | 0.128% | 0.130% |
| Free Valine | 0.144% | 0.118% |
| Total free amino acids | 1.81% | 1.85% |

‡the amounts of the listed free amino-acid residues are provided as the weight percentage based on the total weight of the protein hydrolysate, the protein hydrolysates comprising 4% by weight protein based on the total weight of the protein hydrolysate compositions. The amount of free amino acid residues of the total protein content of HIE 1 or HIE 2 is provided as a weight percentage based on the total weight of the protein content of HIE 1 or HIE 2.

More than fifty percent by weight of the hydrolysed proteins, based on the total weight of protein present in HIE 1 and HIE 2 (i.e. 100% and 87,5%, respectively), are detected as very short chain peptides. "Very short chain peptides" is herein defined as peptides having an amino-acid residues chain length of between about 6 amino acid residues and about 20 amino acid residues.

TABLE 3

Counts of pathogenic bacteria in the enzymatically hydrolysed black soldier fly larvae proteins HIE 1 and in the Maillard reaction products of enzymatically hydrolysed black soldier fly larvae proteins HIE 2

| Microbes cfu/g | HIE 1 | HIE 2 |
|---|---|---|
| Total plate count | 28000 cfu/g | 63000 cfu/g |
| E. coli | <10 cfu/g | <10 cfu/g |
| Salmonella | Not detected in 25 g | Not detected in 25 g |
| B. cereus | <10 cfu/g | <10 cfu/g |
| C. perfringens | <10 cfu/g | <10 cfu/g |

The total plate count, also referred to as 'Aerobic Mesophylic Count 30° C.' (equivalent to ISO 4833), was determined by Nutrilab (Rijswijk, NL); the *Bacillus cereus* count was assessed at 30° C. (equivalent to ISO 7932); the *Clostridium perfringens* count was determined at 37° C. (equivalent to ISO 7937); the *Escherichia coli* plate count was assessed at 44° C.; The *Salmonella* count was assessed using PCR fast method (equivalent to ISO 6579). Thus, in the two products HIE 1 and HIE 2, the microbial count was less than 10 cfu/g protein for *Bacillus cereus*; less than 10 cfu/g protein for *Clostridium perfringens*; less than 10 cfu/g protein for *Escherichia coli*; and the *Salmonella* count was 0 cfu/g protein when 25 g of the HIE 1 or the HIE 2 was assessed. Herewith, the microbial count for both HIE 1 and HIE 2 was within value boundaries that should be reached for application of the larvae water in food products or food ingredients. That is to say, according to the European Commission, in "OECD issue paper on microbial contaminants limits for microbial pest control products", the detected plate counts for the indicated microbes was within acceptable limits according to the European Commission guidelines. See also FIG. 2.

The products resulting from the above process according to the method of the invention, i.e. the enzymatically hydrolysed black soldier fly larvae water-soluble proteins HIE 1 and the Maillard reaction products of enzymatically hydrolysed black soldier fly larvae water-soluble proteins HIE 2, were investigated for sensory parameters, i.e. flavour profile, flavour score, aroma score and bitterness, and compared with aqueous water-soluble protein fraction of black soldier fly larvae. Flavour profiling was descriptive; human respondents (Respondent 1-3) were asked to give the closest comparison to the formed product. For other parameters the product was scored on a scale of 1 (extreme disliking) to 5 (extreme liking) by the three human respondents. The results are indicated in Table 4. To the surprise of the inventors, neither the HIE 1, nor the HIE 2 had a bitter flavour. Adding to the surprise, the initially present insect-like note of the aqueous water-soluble protein fraction of black soldier fly larvae (larvae water) changed towards a meat-like note (resembling the flavour and taste of beef meat) after subjecting the method for providing enzymatically hydrolysed water-soluble insect protein. HIE 2, that was formed as a result of subjecting HIE 1 to the Maillard reaction, had a more pronounced cooked meat flavour compared to HIE 1 and to the larvae water. Surprisingly, the intensity of the meat-like taste of HIE 1 and HIE 2 was several folds higher than the intensity of the meat taste of beef meat itself. Such meat-like flavour of the HIE 1 and the HIE 2 apparently relates to the free amino acid composition of the HIE 1 and the HIE 2.

TABLE 4

Sensory profiling of the aqueous water-soluble protein fraction of black soldier fly larvae (larvae water), the enzymatically hydrolysed black soldier fly larvae proteins HIE 1 and the Maillard reaction products of enzymatically hydrolysed black soldier fly larvae proteins HIE 2 by human respondents (n = 3).

| Parameter (average score)‡ | Aqueous water-soluble protein fraction of black soldier fly larvae (larvae water) | HIE 1 | HIE 2 |
|---|---|---|---|
| Taste | 2.33 | 4 | 4.33 |
| Aroma | 2.67 | 3.33 | 4.33 |
| Bitterness | 5 | 5 | 5 |
| Flavour profile | | | |
| Respondent 1 | Typical insect flavour | Boiled beef | Boiled beef with on sweeter side |
| Respondent 2 | Typical insect flavour | Beef/pork broth | Broth little bit on desirable side |
| Respondent 3 | Typical insect flavour | Ox tail soup | More intense with cooked meat flavour |

‡The three human subjects, referred to as 'Respondent 1-3', scored the sensory parameters Taste, Aroma and Bitterness on an integer scale from 1 to 5, the integers 1-5 having the following meaning: 1. Extremely dislike; 2. Little dislike; 3. Not sure; 4. Little like; and 5. Extremely like. Average values for the individual scores of the three respondents are given.

In view of the sensory profile of HIE 1 and HIE 2, these enzymatically proteolysed black soldier fly larvae water-soluble proteins are suitable for applications such as:

1. pet food flavour enhancer, both for cats and dogs, and more specifically for cats, for which taste plays a central role in food acceptance. Both the free amino acid levels and the total composition of HIE 1 and HIE 2, and in addition the specific intense meat-like profile contribute to the high suitability of the hydrolysates in preparation of feed compositions.
2. aquaculture feed palatant for, for example, farmed marine and fresh water organisms. More specifically, HIE 1 and HIE 2 are suitable as feed additives for feed for shrimps, for which specific free amino acid combinations are already added in the shrimp diet to increase feed acceptability.

3. Constituent of human food preparations. On one hand, humans love to eat meat, on the other hand they are on a mission to reduce animal meat levels in diet. Such a HIE 1 or HIE
4. 2 formulation enhances the appeal of human food by imparting meat-like flavour. Microbial counts in the product (see Table 3) also indicate that the product is within safe microbial counts for human consumption.
5. additive or constituent of feed for farmed animals. Weaning and post weaning animals (especially pets and also weaning pigs, post-hatching poultry and fishes) struggle with stomach disorders, because of problems in digestion of complex foods. HIE 1 and HIE 2 have high amounts of proteins with a molecular mass of smaller than 1000 Da (See Table 2). These proteins are easily and highly digestible. This is also indicated by the high pepsin digestibility (refer to Table 2). Such a product with such a relatively high digestibility 100%) is beneficially used as nutritional supplements for young animals. Indeed, inclusion of a certain amount (e.g. 2-8%) animal-protein hydrolysates (e.g., porcine intestine, porcine mucosa, salmon viscera, or poultry tissue hydrolysates) or soybean protein hydrolysates in practical corn- and soybean meal-based diets can ensure desirable rates of growth performance and feed efficiency in weanling pigs, young calves, post-hatching poultry, and fish (Hou et al., 2017). Herewith, such mammal/fish/poultry-based protein hydrolysates hold promise in optimizing the nutrition of domestic and companion animals, as well as their health (particularly gut health) and well-being.

Examples—Sensory Trials (Blinded Human Consumers)

Example 1. Blind Human Trials (Application of HIE 1 in a Noodle Recipe)

From the initial tasting tests of the products HIE 1 and HIE 2 (see here above), it was apparent that hydrolysed insect extract 1 and hydrolysed insect extract 2 both had a beef-meat like flavour. Therefore, the objective of Example 1 was to study the effect of replacing the beef or beef flavour components in beef noodles by hydrolysed insect extract 1, in sensory acceptance testing.

TABLE A

Recipe used for testing

| Ingredient | Control recipe | Test recipe comprising HIE 1 |
| --- | --- | --- |
| Cubed beef stew meat | 0.45 kg | — |
| Chopped onion | 1 cup | 1 cup |
| Chopped celery | 1 cup | 1 cup |
| Beef bouillon granules | ¼ cup | — |
| Dried parsley | ¼ cup | ¼ cup |
| Ground black pepper | 1 pinch | 1 pinch |
| Chopped carrots | 1 cup | 1 cup |
| Water | 5.75 cup | 5 cup |

Materials and Methods

A 4.5/5 rated recipe was chosen from allrecipes.com (Loop, n.d.). All the ingredients were sourced from local supermarket. The details of the ingredients are mentioned in Table A. In the Test recipe, beef stew meat and beef granules were replaced by hydrolysed insect extract 1, HIE 1.

Both recipes were produced in a large sauce pan. For Control recipe meat, onion and celery were heated for 5 min. at medium high heat (or until meat turned brown on all sides). Other ingredients were stirred in and boiled at low heat and simmer for 30 minutes. For the Test recipe onions and celery were heated for 5 min. at the same heat level, until they turned brown. Following which parsley, pepper, carrots, water, hydrolysed insect extract 1 and egg noodles were added. Product was cooked at low heat, simmered for 30 min.

Beef cubes were removed from the Control recipe, to avoid bias behaviour of sensory respondents. Sensory panel consisted of six members (all aged between 25 to 40 years). Hundred g portion of each noodle soup was provided blinded to each respondent. Water was provided in a cup to each respondent for washing the taste pallets between two tasting. Acceptance testing was considered using a hedonic scale of 9 points (9-extremely like, 5-neither like or dislike and 1-extremely dislike).

Results and Discussion

The blind sensory response of the respondents is marked in the Table B. The Respondents were provided with a portion of the Control recipe and a portion of the Test recipe in a blinded fashion: the Respondents were not notified beforehand whether they were eating Control recipe, or Test Recipe, and in which order.

TABLE B

| Sensory score | | |
| --- | --- | --- |
| Human Respondent | Control recipe | Test recipe |
| R1 | 6 | 8 |
| R2 | 4 | 7 |
| R3 | 5 | 9 |
| R4 | 7 | 8 |
| R5 | 6 | 6 |
| R6 | 5 | 7 |
| Average score + SD | 5.5 ± 1.0 | 7.5 ± 1.0 |

All respondents liked the Test recipe. This was also visible from the average score. Test recipe had a significantly better taste than control recipe (t-test, $p<0.05$). Most respondents blindly indicated that the Test recipe had a more beef flavour in comparison to Control recipe.

Conclusion

The results of the noodle test show that hydrolysed insect extract 1 (HIE 1) is suitable as a food ingredient in food preparations and that the HIE 1 enhances or even imparts beef-like meat flavour to the food product, e.g. the noodles tested.

Example 2—Flavour Enhancement Potential of Hydrolysed Insect Extract 2 (HIE 2) in a Non-Meat Preparation Materials and Methods A 4.5/5 rated recipe of Quinoa Black Bean Burgers was chosen from allrecipes.com (DownHomeCitySisters, n.d.; accessed September 2019). All ingredients were purchased from a local supermarket. The base recipe composition was made using the ingredients mentioned in Table 5. Quinoa was boiled in water, then simmered at medium heat until all water was absorbed and the quinoa was soft. Black beans were mashed into a paste. Following this all the ingredients were mixed in a bowl. The mixture was divided into two equal portions. Control portion of the composition referred to as base recipe was mixed with 12.5 g water, while a test portion of the base recipe composition was mixed with 12.5 g of hydrolysed insect extract 2 (HIE 2), which was previously 5 times concentrated (protein content was about 20% by weight based on the total weight of the HIE 2). Both portions were allowed to marinade for 1 h at 4° C. Following this step, small burgers of 2.5 cm diameter (approximate) were made from both control recipe and test recipe. These burgers were fried in olive oil (using a low flame) until a dark golden crust was obtained.

TABLE 5

Ingredients in base recipe

| Ingredient | Base recipe |
|---|---|
| Canned black beans (rinsed) | 0.42 kg |
| Quinoa | ¼ cup |
| Water | ½ cup |
| Bread crumbs | ½ cup |
| Yellow bell pepper | ¼ cup |
| Minced onions | 2 tablespoons |
| Minced garlic | 1 clove (large) |
| Ground cumin | 1.5 teaspoon |
| Salt | 0.5 teaspoon |
| Hot pepper sauce | 1 teaspoon |
| Egg | 1 |
| Olive oil (to fry) | 3 tablespoon |

The sensory panel ('respondents') consisted of seven human members (all aged between 25 and years). Each respondent was provided blindly with a burger from the test recipe comprising HIE 2 and the control recipe. Thus, the respondents did not know which burger was the control recipe and which burger was the test recipe. Water was provided in a cup to each respondent for washing the taste pallets between two tastings. Acceptance testing was considered using a hedonic scale of 5 points (5-extremely like, 3-neither like nor dislike, and 1-extremely dislike).

Results and Discussion

The sensory response of the respondents in marked in the Table 6.

TABLE 6

Sensory score

| Respondent | Control recipe | Test recipe (HIE 2) |
|---|---|---|
| R1 | 3.5 | 5 |
| R2 | 3 | 5 |
| R3 | 3.5 | 4 |
| R4 | 4 | 5 |
| R5 | 3 | 5 |
| R6 | 3 | 4 |
| R7 | 3 | 5 |
| Average score + SD | 3.2 ± 0.39 | 4.7 ± 0.48 |

As visible from the scorecard in Table 6, all respondents preferred the test recipe (containing hydrolysed insect extract 2) over control recipe. Test recipe was significantly better in taste than control recipe (t-test, $p<0.05$). All the respondents indicated that the test recipes tastes like beef. Some respondents also indicated that the test recipe not only had strong meat flavour, but also that the spice flavour was better compared to the control recipe.

Conclusion

From the above blinded test, it is concluded that hydrolysed insect extract 2 efficiently and satisfactorily imparts meat flavour, i.e. beef meat flavour, in vegetarian preparations. In the HIE 2 comprising composition, the presence of the HIE 2 also enhances the flavour of other ingredients in the test recipe. Herewith, application of the HIE 2 protein hydrolysate as a flavour and/or flavour enhancing food ingredient in non-meat food-products, has the potential to reduce the meat consumption (beef, pork and poultry), which reduction of meat consumption would contribute to sustainable farming and food production and food consumption. It is now due to the invention that larvae protein hydrolysates are added to the currently limited arsenal of sustainable proteins sources (such as vegetable proteins), since application of e.g. HIE 1 and HIE 2 hydrolysates as a food product ingredient enhances the animal meat flavour in such food preparations to a beneficial extent suitable for mass production and mass consumption by humans.

Example 3

2. Materials and Methods 2.1. Reagents

All the reagents were of analytical grade. Dimethylsulfoxide, methanol, ethanol, calcium chloride, potassium chloride, sodium chloride, hydrogen peroxide and Tween-20 were purchased from Merck (VWR, Leuven, Belgium). Sodium nitrite, bovine serum albumin, phorbol 12-myristate 13-acetate and Percoll™ were purchased from Sigma (Bornem, Belgium). Aqueous extracts and solutions were made in Milli-Q water obtained using Milli-Q water system (Millipore, Bedford, USA). Bicinchoninic acid and copper (II) sulfate solutions were purchased from Sigma (Steinheim, Germany). Whatman filter paper grade 4 (270 mm) was purchased from Amersham (Buckinghamshire, UK). Sterlip 30 ml disposable vacuum filter system was purchased from Millipore (Bedford, USA). 2,2-Diphenyl-1-picrylhydrazyl and 2'-azino-bis(3-ethylbenzthiazoline-6-sulfonic acid) were purchased from Aldrich (Darmstadt, Germany). 8-amino-5-chloro-7-phenylpyrido[3,4-d]pyridazine-1,4(2H,3H)dione (L-012) was purchased from Wako Chemicals (Neuss, Germany).

2.2. Raw Materials

Chicken meal (CM) and fish meal (FM) were purchased from an online webshop in September 2019. The chemical composition of both ingredients as declared by the supplier is indicated in table 7.

TABLE 7

Chemical composition of chicken meal and fishmeal (as in basis, provided by supplier).

| Nutrients | Chicken meal | Fish meal |
|---|---|---|
| Moisture (g/kg) | 60.0 | 100.0 |
| Crude protein (g/kg) | 700.0 | 710.0 |
| Crude fat (g/kg) | 120.0 | 120.0 |
| Added antioxidant | No | Yes (E324) |
| Form | Powder | |

A puree of BSF larvae, also referred to as BSF PureeX™ (BSF-P), was prepared by Protix B.V. (*Dongen, The Netherlands*) *in October* 2019. The puree was obtained according to the following method. Live and washed Black Soldier Fly larvae of 14 days old were collected just before being subjected to the mincer for mincing the larvae (therewith providing larvae pulp), and subsequently stored at 4° C. until used. For each experiment, larvae were minced freshly. The minced larvae was subjected to a separation step, obtaining water-soluble BSF larvae protein according to the invention. The water-soluble BSF larvae protein was treated with 1 wt % Flavourzyme, based on the mass of the protein, for 6 hours at 50° C. (±2° C.) under continuous stirring, according to the method of the invention. Flavourzyme (Novozymes, Denmark) is a combination of aminopeptidases which have endopeptidase and exopeptidase activities. The enzyme-treated water-soluble BSF larvae protein was heated subsequently, for inactivation of the enzyme, according to the method of the invention.

The aqueous protein hydrolysates (BSF-APH) obtained as here above described, was provided by Protix B.V. (*Dongen, The Netherlands*) *in October* 2019. According to Protix: BSF-APH is a hydrolysate of water soluble BSF proteins, prepared according to the method of the invention. It is established that BSF-APH has high solubility in water (>95%). The chemical composition of all three ingredients as declared by the supplier or by Protix (the inventors) is indicated in table 8.

TABLE 8

Chemical composition of BSF protein derivative BSF-APH (as in basis, prepared by Protix).

| Nutrients | BSF-APH[3] |
|---|---|
| Moisture (g/kg) | 55[a] |
| Crude protein (g/kg) | 455[a] |
| Crude fat (g/kg) | 35[a] |
| Added antioxidant | No |
| % of total proteins <1000 Da | >98 |
| Form | Powder |

[3]BSF-APH: BSF aqueous protein hydrolysate;
[a]Mean values based on the range determined by Protix.

Water soluble extracts were prepared for CM and FM. These products (100 g each) were dissolved with six times volumes of Milli-Q water based on their respective dry matter contents and stirred for 2 h on a magnetic stirrer. Post centrifugation (1000×g for 30 min at 4° C.), the top fat layer was removed and the supernatant was filtered using Whatman Filter (grade 4). The centrifugation and filtration step was repeated again to remove all non-soluble residues. Finally the supernatant was filtered using a Sterlip Filter (50 mL, 0.22 μm) and freeze dried over a period of two days to obtain respective water soluble extract powders. BSF-APH was used directly because it has water solubility >95%. All four water soluble extract and BSF-APH powders were stored in a desiccator (at 18° C.) until further use.

2.3. Protein Quantification

Total protein content of four water soluble extracts and BSF-APH powders was analysed using Bicinchoninic acid (BCA) protein assay [24]. The calibration curve was obtained using bovine serum albumin (BSA) as standard at concentrations: 0, 0.125, 0.25, 0.5 and 1 mg/ml. Stock solutions of 3 mg/ml water soluble extracts and BSF-APH were used for analysis. A test solution was made by dissolving 4900 μl BCA (49/50) and 100 μl copper (II) sulfate (1/50). Sample stock solutions (10 μl) and test solution (200 μl) were added in wells of 96-well plate. This plate was incubated at 37° C. for 30 min and absorbance was measured at 450 nm using a Multiscan Ascent (Fisher Scientific, Asse, Belgium).

2.4. DPPH Assay

DPPH radical scavenging activity was analysed according to protocol of Brand-Willams et al. RN, with some modifications. *DPPH test solution was made by dissolving* 10.5 mg DPPH in 40 ml ethanol. Test solution was made fresh and stored in dark until further use. DPPH working solution was made by diluting test solution with 10 times ethanol (to obtain absorbance of 0.6 to 0.8 at 517 nm). DPPH working solution (1920 μl) was mixed with 20 μl of samples dilutions (four water soluble extracts and BSF-APH in Milli-Q water) to obtain final concentration of 0.0125, 0.025, 0.05, 0.1 and 0.2 mg/ml. The decrease in absorbance after 30 and 60 min of incubation in dark was recorded at 510 nm using HP 8453 UV-vis spectrophotometer (Agilent Technologies, Waldbronn, Germany). Instead of sample dilutions only Milli-Q water was used in case of control.

2.5. ABTS Assay

ABTS cation radical scavenging activity was analysed according to protocol of Arnao et al. [26], with some modifications. ABTS test solution was made by dissolving 7.0 mmol/l ABTS and 2.45 mmol/l potassium persulfate in Milli-Q water. The test solution was kept overnight in dark at room temperature. ABTS working solution was made by diluting with methanol to obtain the absorbance between 0.7 and 0.8 at 734 nm. ABTS working solution (1920 μl) was mixed with 20 μl of samples dilutions (four water soluble extracts and BSF-APH in Milli-Q water) to obtain final concentration of 0.0125, 0.025, 0.05, 0.1 and 0.2 mg/ml. The decrease in absorbance after 30 min of incubation in dark was recorded at 734 nm using HP 8453 UV-vis spectrophotometer (Agilent Technologies, Waldbronn, Germany). Instead of sample dilutions only Milli-Q water was used in case of control.

2.6. Myeloperoxidase (MPO) Activity Using Specific Immunological Extraction Followed by Enzymatic Detection (SIEFED) Assay SIEFED assay is a licensed method developed by Franck et al. [27] for specific detection of animal origin MPO. MPO solution was made by diluting human MPO in 20 mM phosphate buffer saline (at pH 7.4), 5 g/l BSA and 0.1% Tween-20. Sample dilutions at final concentration of 0.0125, 0.025, 0.05, 0.1 and 0.2 mg/ml were incubated for 10 min (at 37° C.) with MPO solution at a final concentration of 25 ng/ml. After incubation, the mixtures were loaded into the wells of a 96 wells microtitre plate coated with rabbit polyclonal antibodies (3 μl/ml) against equine MPO and incubated for 2 h at 37° C. in darkness. After washing up the wells, the activity of the enzymes captured by the antibodies was measured by adding hydrogen peroxide (10 μM), $NO_2^-$ (10 mM) and Amplex™ Red (40 μM). The oxidation of Amplex™ Red into the fluorescent adduct resorufin was monitored for 30 min at 37° C. with Fluorosckan Ascent (Fisher Scientific, Asse, Belgium). Instead of sample dilutions only Milli-Q water was used in case of control.

2.7. Myeloperoxidase (MPO) Activity Using Classical Measurement

MPO solution was prepared as mention in section 2.6. Sample dilutions at final concentration of 0.0125, 0.025, 0.05, 0.1 and 0.2 mg/ml were incubated for 10 min (at 37° C.) with MPO solution at a final concentration of 25 ng/ml. After incubation, the mixture (100 µl) was immediately transferred into 96-well microtitre µlate. This was followed by addition of 10 µl $NO_2$-(10 mM) and 100 µl of Amplex™ Red and hydrogen peroxide mixture (at concentrations mentioned in section 2.6). The oxidation of Amplex™ Red into the fluorescent adduct resorufin was monitored for 30 min at 37° C. with Fluorosckan Ascent (Fisher Scientific, Asse, Belgium) immediately after addition of relevation mixture. Instead of sample dilutions only Milli-Q water was used in case of control.

2.8. Cellular Antioxidant Activity

Preparation of the neutrophil and phorbol 12-myristate 13-acetate (PMA) solutions were made according to Paul et al. [17]. Neutrophil response modulation activity of samples was analysed using the protocol of Tsumbu et al. [16]. Neutrophil suspension (1 million cells/143 µl PBS) was loaded in wells of 96-wells microtite µlate and incubated for 10 min (at 37° C. in dark) with phospahte buffer saline solution of samples at final concentrations of 0.0125, 0.025, 0.05, 0.1 and 0.2 mg/ml. After incubation, 25 µl calcium chloride (10 µM) and 20 µl L-012 (100 µM) were added in wells. The neutrophils were activated with 10 µl PMA (16 µM) immediately before monitoring the chemiluminesence response of neutrophils during 30 min at 37° C. using Fluorosckan Ascent (Fisher Scientific, Asse, Belgium). Instead of sample dilutions only phosphate buffer saline was used in case of control.

2.9. Statistical Analyses

All the analyses were performed in triplicates. For protein quantification, the equation of a fitted line and R-square value were calculated using linear regression. The relationships between concentration and inhibition obtained for antioxidant assays were non-monotonic in nature. To address this, the locally estimated scatterpot smoothing (LOESS) regression technique was used to model the relationship [28]. Models were fitted using the R statistical software [29]. These models require a span parameter that defines the smoothing sensitivity of the local regressions. By visual inspection a span parameter value of 0.4 was found to be suitable for all concentration and inhibition relationship curves. Concentrations with a predicted inhibition percentage of interest, such as $IC_{50}$ (concentration at which 50% inhibition is reached), were found using the fitted models in combination with a numerical search routine.

3. Results

3.1. Protein Quantification

The calibration curve obtained using BSA, equation of the line and R-square value are established. The optical density of samples and relative concentration of proteins (calculated using equation of line) are mentioned in table 9. CM extract solution (3 mg/ml) exhibits the highest, on the other hand BSF-APH solution exhibits the lowest protein concentrations amongst the tested solutions using Bicinchoninic acid assay.

TABLE 9

Protein quantification using Bichinchoninic acid assay

| Product | Product used for testing in all the assays | Mean optical density | Protein concentration (mg/ml) |
|---|---|---|---|
| BSF-APH[3] | Product as produced by Protix | 0.383 | 0.702 |
| FM[4] | Water soluble extract | 0.425 | 0.829 |
| CM[5] | Water soluble extract | 0.481 | 0.998 |

[3]BSF-APH: BSF aqueous protein hydrolysate;
[4]FM: Fish meal;
[5]CM: Chicken meal.

3.2. DPPH Assay

DPPH radical scavenging activity of all five samples after 30 and 60 minutes of incubation is indicated in FIG. 3 and FIG. 4, respectively. The µlot shows the measured values as well as fitted curves obtained from LOESS. CM exhibited pro-oxidant behavior at all tested concentrations after as well as 60 minutes of incubation. Whereas, FM exhibited pro-oxidant behavior at four out of five tested concentrations after 30 min of incubation and at all tested concentrations after 60 min of incubation. It was not possible to calculate $IC_{50}$ for all samples (after 30 or 60 min of incubation) because the samples either exhibited pro-oxidant activity or 50% inhibition was not achieved during the assay. The $E_{max}$ (maximum inhibition achieved during the assay) of all the samples are also indicated in table 11 and are in following order: BSF-APH>FM after 30 minutes of incubation.

TABLE 10

Antioxidant activity $IC_{50}$ (mg/ml) of samples obtained using different assays

| Assay | BSF-APH[3] | FM[4] | CM[5] |
|---|---|---|---|
| DPPH 30 min | NE[c] | NE[c] | PO[d] |
| DPPH 60 min | NE[c] | PO[d] | PO[d] |
| ABTS 30 min | 0.03 | 0.11 | 0.09 |
| MPO[a] SIEFED | 0.18 | PO[d] | PO[d] |
| MPO[a] Classical | 0.05 | PO[d] | PO[d] |
| CAA[b] | NE[c] | NE[c] | NE[c] |

[3]BSF-APH: BSF aqueous protein hydrolysate;
[4]FM: Fish meal;
[5]CM: Chicken meal;
[a]MPO: Myeloperoxidase;
[b]CAA: Cellular antioxidant activity using neutrophil model;
[c]NE: Not estimated because 50% inhibition was not achieved in tested concentrations;
[d]PO: Not estimated because sample exhibited pro-oxidant activity on tested concentrations.

TABLE 11

Antioxidant activity $E_{max}$ (% inhibition) of samples obtained using different assays

| Assay | Parameter | BSF-APH[3] | FM[4] | CM[5] |
|---|---|---|---|---|
| DPPH 30 min | Emax (%) | 16.26 | 0.75 | PO[c] |
| | C* (mg/ml) | 0.20 | 0.03 | — |
| DPPH 60 min | Emax (%) | 17.75 | PO[c] | PO[c] |
| | C* (mg/ml) | 0.20 | — | — |
| ABTS 30 min | Emax (%) | 90.81 | 70.40 | 69.39 |
| | C* (mg/ml) | 0.20 | 0.20 | 0.20 |

TABLE 11-continued

Antioxidant activity $E_{max}$ (% inhibition) of samples obtained using different assays

| Assay | Parameter | BSF-APH[3] | FM[4] | CM[5] |
|---|---|---|---|---|
| MPO[a] SIEFED | Emax (%) | 53.08 | PO[c] | PO[c] |
| | C* (mg/ml) | 0.20 | — | — |
| MPO[a] Classical | Emax (%) | 90.86 | PO[c] | PO[c] |
| | C* (mg/ml) | 0.20 | — | — |
| CAA[b] | Emax (%) | 36.62 | 21.81 | 5.08 |
| | C* (mg/ml) | 0.20 | 0.05 | 0.20 |

*C: Concentration at which Emax is achieved;
[3]BSF-APH: BSF aqueous protein hydrolysate;
[4]FM: Fish meal;
[5]CM: Chicken meal;
[a]MPO: Myeloperoxidase;
[b]CAA: Cellular antioxidant activity using neutrophil model;
[c]PO: Not estimated because sample exhibited pro-oxidant activity on tested concentrations.

3.3. ABTS Assay

ABTS cation radical scavenging activity of samples after 30 minutes of incubation is shown in FIG. (measured values as well as fitted curves obtained from LOESS). All the samples exhibited a similar inhibition pattern i.e., % inhibition increased as a function of increasing concentration. The $IC_{50}$ of samples are mentioned in table 10 and are in following order: FM>CM>BSF-APH. Lower the $IC_{50}$, higher is the ABTS cation radical scavenging activity. The $E_{max}$ (maximum inhibition achieved during the assay) of all the samples are indicated in table 11 and are in following order: BSF-APH>FM>CM.

3.4. Myeloperoxidase (MPO) Activity Using Specific Immunological Extraction Followed by Enzymatic Detection (SIEFED) Assay MPO response modulation activity of samples obtained using SIEFED assay is shown in FIG. 6 (measured values as well as fitted curves obtained from LOESS). The $IC_{50}$ of samples are mentioned in table 10. The $E_{max}$ of samples are shown in table 11. FM and CM show pro-oxidant behavior at all tested concentrations.

3.5. Myeloperoxidase (MPO) Activity Using Classical Assay

MPO response modulation activity of samples obtained using classical assay is indicated in FIG. 7 (measured values as well as fitted curves obtained from LOESS). CM and FM exhibited pro-oxidant behavior at all tested concentrations. The $E_{max}$ of all the samples tested are indicated in table 11. BSF-APH exhibited $E_{max}$>75%. The $IC_{50}$ of samples are mentioned in table 10.

3.5. Cellular Antioxidant Activity

Neutrophil response modulation activity (measured values as well as fitted curves obtained from LOESS) and $E_{max}$ of samples are shown in FIG. 8 and table 11, respectively. All the tested samples exhibited $E_{max}$>0%. BSF-APH, FM and CM exhibited $E_{max}$<40%. CM exhibited pro-oxidant behavior at 3 out of 5 tested concentration. The $IC_{50}$ of samples are mentioned in table 10.

4. Discussion 4.1. Protein Quantification

The protein concentration of BSF-APH and two water soluble extracts estimated using Bichinchoninic acid assay are displayed in table 9. For BSF-APH, 3 mg/ml solution resulted in protein concentration of 0.702 mg/ml, which translates into 0.235 mg proteins per gram of BSF-APH (or 23.5% proteins). According to the inventors (Protix), the average protein content of BSF-APH is 45.5% (see table 8, analyzed using Dumas method). Differences in protein content arise due to method of analysis. Bichinchoninic acid assay is based on the detection of bonds specific to Cys, Trp and Tyr. On the other hand, Dumas assay is based on estimation of total organic nitrogen. Therefore, protein content estimated using Dumas method is always higher than that estimated using Bichinchoninic acid assay. However, comparing the two protein estimation methods is not an aspect of the current invention. Considering the amino acid pattern similarities between FM and CM, it is concluded that protein content of two water soluble extracts are in following order: CM>FM>45.5%.

4.2. DPPH Radical Scavenging Activity

DPPH and ABTS assays are commonly used to analyze antioxidant potential of food and feed products. DPPH radical scavenging activity represents the ability of a sample to donate hydrogen atom (referred as hydrogen atom transfer) or electrons (referred as single electron transfer) to stabilize free radicals. DPPH assay $IC_{50}$ and $E_{max}$ for all tested samples are mentioned in table 10 and table 11, respectively. Post 30 min of incubation, all the tested samples exhibit $E_{max}$<50% BSF-APH contain at least 98% proteins <1000 Da. The inventors were not able to find any representative literature for molecular weight distribution of FM and CM. However, according to the literature, FM and CM contain 2.2% and 1.1% free amino acid (of total proteins), respectively [Li, P.; Wu, G. Composition of amino acids and related nitrogenous nutrients in feedstuffs for animal diets. Amino Acids 2020, 1-20, doi:10.1007/s00726-020-02833-4.]. Which translates into FM and CM containing at least 2.2% and 1.1% proteins <1000 Da respectively. The capacity of proteinaceous materials to scavenge free radicals depends on the protein molecular weight distribution. Proteins with low molecular weight peptides could scavenge free radicals more efficiently. However, this does not explain the fact that BSF-APH contains higher amount of proteins <1000 Da and still exhibits lower inhibition of DPPH free radicals. Free radical scavenging activity of proteinaceous molecules is also influenced by: (1). Amino acid composition: hydrophobic amino acids (for e.g. Tyr, Phe, Pro, Ala, His and Leu) have superior radical scavenging activity in comparison to hydrophilic amino acids; (2). Amino acid sequence: Peptides with amphiphilic nature could enhance radical scavenging activity of a sample. Chemical analyses have indicated that Tyr exhibit antioxidant behavior via hydrogen atom transfer mechanism. On the other hand, amino acids such as Cys, Trp and His exhibit antioxidant behavior via single electron transfer mechanism.

FM and CM exhibit pro-oxidant behavior at most concentrations tested after 30 min as well as 60 min of incubation (see FIGS. 3 and 4). This behavior mainly arises from the thermal processing. For both FM and CM, thermal processing commonly involves heating the raw product at high temperatures for 15 to 20 min. In Norway, during fishmeal production, wild caught fishes are subjected to heating at temperatures 70° C. for time min in order to achieve 100 logic) reductions of Enterobacteriaceae and Salmonella counts. Such strict thermal processing conditions may result in oxidation of fats and proteins. Fishmeal contains lipids rich in polyunsaturated fatty acids that are more susceptible to thermal oxidation. Antioxidant are commonly added in fishmeal to prevent the oxidation of polyunsaturated fatty acids (also visible in table 7). Heat induced oxidation of amino acids lead to development of wide range oxidation products. The pro-oxidant behavior of amino acid oxidation by products is already known. They can result in a wide range of health conditions in animal body. According to the supplier, all the black soldier fly protein derivatives used in this study were thermally processed at temperatures <100° C. for time <1.5 min. Supplier also indicated that these thermal processing time-temperature combinations were adopted to ensure minimum damage to nutrients (proteins and fat) and adequate inactivation of pathogenic microbiota. This implies that pro-oxidant behavior of FM and CM arises mainly due to stringent production method.

4.3. ABTS Cation Radical Scavenging Activity

ABTS cation radical scavenging denotes the ability of sample to donate electron and stabilize free radicals. ABTS assay 1050 of all samples are indicated in table 10. They are in following order: FM>CM>BSF-APH. The higher the $IC_{50}$, the lower the antioxidant activity. In this assay even FM and CM exhibit antioxidant activity. It appears that FM and CM extracts may be efficient where free radical(s) could be stabilized using single electron transfer mechanism. However, they still exhibit lower scavenging activity in comparison to BSF-APH.

BSF-APH has at least 98% proteins <1000 Da (the lowest protein molecular weight amongst all tested sample) and also exhibited lowest ABTS $IC_{50}$. Dependence of radical scavenging activity on protein molecular weight is already explained in section 4.2.

Zhu et al. developed BSF protein hydrolysate using wide range of commercial enzymes. The hydrolysates were further fractionated into following group: group 1 (<3000 Da), group 2 (3000 to 10,000 Da) and group 3 (>10,000 Da) using ultrafiltration. The activity of these hydrolyzed fractionates were also investigated for ABTS cation radical scavenging activity. Ascorbic acid was used as the reference molecule in this study. Interestingly the best performing fractionate and ascorbic acid were able to inhibit 85.67% and 92.11% of ABTS cation radical at 0.05 mg/ml concentration, respectively. The inventors now established that BSF-APHs exhibit ABTS cation radical scavenging $E_{max}$ of 91% (at 0.2 mg/ml). This shows that fractioning BSF-APH will result in fractions that have very strong antioxidant potential.

4.4. Neutrophil Response Modulation Activity

Strong free radical scavenging activities of BSF derivatives are evident from section 4.2 and 4.3. Furthermore, all the samples were also tested for neutrophil response modulation activity. Neutrophils are white blood cells present in animal body (including humans, pets, fishes, poultry and swine). They are involved in the primary defense against pathogens. When pathogenic microbes enter the animal body, neutrophils rush to the site of infestation and initiate defense. During granulation, neutrophil release a wide range of oxidative enzymes including NADPH oxidase, which is responsible for production of superoxide anion and by product (e.g. hydrogen peroxide). Superoxide anion can further react with nitric oxide radical to produce peroxynitrite. This process also generates hydroxyl radical (by reaction of hydrogen peroxide with metal ion). This battery of oxidative reactions are crucial to the defense of the host animal. However, these ROS generated during host defense can react with enzymes, proteins, lipids, etc. of body cells and result in the development of different health conditions (for e.g. cellular ageing, cancer, etc.). The neutrophil assay conducted in this research determines the ability of proteinaceous molecules to scavenge ROS produced as a result of neutrophil activity. PMA was used to activate protein kinase C present in neutrophils, which results in production of NADPH oxidase responsible for catalyzing ROS production. ROS production in system is coupled with lucigenin amplified chemiluminescence. Ability of proteinaceous sample to scavenge ROS (particularly superoxide anion) is marked by decreased chemiluminescence. To the inventor's knowledge, this is the first analysis and determination of in vitro neutrophil response modulation activity of BSF derivatives. CM exhibited pro-oxidant behavior at 3 out of 5 tested concentrations, and $E_{max}$ of only 5% at 0.2 mg/ml (see FIG. 8 and table 11). CM is commonly used in pet food preparations. However, the inventors now established that CM inclusion offers little or no benefits relating to scavenging the ROS produced by neutrophils, in contrast to the scavenging activity of the hydrolysate of the invention. Moreover, CM inclusion could even result in inflammatory damage to host cells, in contrast to the BSF larvae protein hydrolysate of the invention. Repetitive inflammatory damage of canine or feline cells could translate into conditions such as accelerated aging, slow cognitive function, etc..

On the other hand, FM exhibits mild antioxidant behavior in this assay, with $E_{max}$ of 22% (see table 11). At 0.2 mg/ml, FM exhibits inhibition of 5%. Aquaculture rearing media (i.e. water) offers a continuous buffer of pathogenic bacteria. Therefore, aquaculture organisms are at constant risk of pathogenic bacterial invasions. This results in wide range of health conditions, including reduced immunity, aging, etc. The inventors executed comparative tests with FM which highlights the inadequacy of FM to suppress the inflammatory damage from repetitive neutrophil activity. This often translates into incremental cost occurring as a result of antibiotics and nutritional supplement usage. Surprisingly, BSF-APH exhibits $E_{max}$ of 36.62% (see table 11). Therefore, without wishing to be bound by any theory, according to the inventors, the BSF-APH of the invention offers natural and sustainable solution to suppress oxidative damage resulting from pathogenic invasion.

4.5. MPO Response Modulation Activity (SIEFED and Classical Assay)

The general mechanism of neutrophil response is known. The neutrophil extracellular trap contains several molecules required to inactivate pathogenic microbes. MPO enzyme present in neutrophil extracellular trap can produce hypochlorous acid from hydrogen peroxide and chloride ion. Additionally, MPO is capable of oxidizing tyrosine into the tyrosyl free radical. Both products of MPO oxidation (hypochlorous acid and tyrosyl free radical) are crucial to inactivate pathogens. Again, repetitive interaction of these molecules with animal cells result in inflammatory damage. In an animal body, MPO—Fe(III) (active form) reacts with hydrogen peroxide to form oxoferryl π cation radical (CpI form). CpI form converts back into MPO—Fe(III) coupled with chloride ion transforming into hypochlorous acid.

However, in the present experiment, back reduction of the Cpl form to MPO—Fe(III) was achieved in 2 stages. First reduction of Cpl to MPO—Fe(IV)=O via electron transfer through nitrite ions. Then, electron provisioning was done (via Amplex™ Red oxidation to resorufin reaction) which converts MPO—Fe(IV)=O to MPO—Fe(III) form. Proteinaceous molecules could prevent the oxidative damage resulting from MPO either by directly reacting with Cpl form and terminating the halogenation, or by donating hydrogen (hydrogen atom transfer) to ROS produced as a consequence of MPO activity. MPO response modulation activity was analyzed using the classical and SIEFED assay. The classical assay measures ability of sample to complex with Cpl form and stabilize ROS. Whereas in SIEFED assay, MPO is bound to rabbit polyclonal antibodies (and rest of the compounds are washed away), so it purely measures the ability of samples to complex with Cpl form.

As with neutrophil response modulation activity, MPO response modulation activity of the BSF derivative hydrolysed BSF larvae protein is also found by the inventors for the first time. FM and CM exhibit pro-oxidant behavior in both the assays (see FIGS. 6 and 7). Presence of oxidative reaction products in FM and CM (as a consequence of production process) that are capable of initiating pro-oxidative response has been already discussed in section 4.2. Detailed in vitro investigations in comparative examples realized by the inventors show that inclusion of FM and CM in animal diets may result in inflammatory damage, in contrast to the effect seen with BSF-APH.

In classical assay, BSF-APH exhibits surprisingly strong antioxidant potential. BSF-APH shows strong antioxidant potential in classical assay (see table 10). These observations show that BSF-APH is very suitable for use in pet food and aquaculture formulations to effectively suppress inflammatory damages resulting from MPO activity, for example for use as a food or feed ingredient.

The inventors surprisingly found that BSF protein derivatives offer anti-oxidative advantage over FM and CM.

Example 4

Protein Hydrolysate—Cat Palatability Testing

Introduction

Protein Hydrolysate was prepared according to the method of the invention, providing protein hydrolysate of the invention, i.e. the enzymatically hydrolysed black soldier fly larvae proteins HIE 1 (details for preparing HIE 1 are for example outlined in Example 1, here above). The protein hydrolysate applied in example 4 contained 100% of proteins with a molecular weight of below 1000 Da (short chain peptides). Additionally, up to 45% of the proteins in the protein hydrolysate are present in form of free amino acids.

Both short chain peptides and free amino acid residues (depending on amino acid composition and arrangement) can impart flavour to pet food preparations. Example 4 provides the evaluation of the flavour enhancement potential of the Protein Hydrolysate HIE 1 in cat food preparation.

Materials

The cat food palatability testing was conducted at firm De Morgenstond (Dussen, The Netherlands). Protein Hydrolysate HIE 1 was prepared and provided by the inventors. Two commercially available cat food palatability enhancers (referred to as "flavour A" and "flavour B") were provided by a top flavour company. These cat food palatability enhancers consist of a solution of hydrolysed proteins (Givaudan, The Netherlands). Purina Felix (wet cat food) with very mild concentrations of palatability enhancer was sourced locally.

Methods

The Protein Hydrolysate HIE 1 powder was dissolved in water to make 25% end solution based on the dry matter (which was used for testing). Flavours A and B were already supplied as liquid. Doses of palatability enhancer used in this study of Example 4 are mentioned in Table 12.

TABLE 12

Dose of commercially available Palatability Enhancers flavour A and flavour B and HIE1

| Test set-up 1 | |
| --- | --- |
| Recipe 1.1 | Recipe 1.2 |
| Felix (wet- mild palatant added by manufacturer) + 1.25% Protein Hydrolysate HIE 1 of the invention | Felix (wet- mild palatant added by manufacturer) + 1% Flavour A |
| Test set-up 2 | |
| Recipe 2.1 | Recipe 2.2 |
| Felix (wet- mild palatant added by manufacturer) + 1.25% Protein Hydrolysate HIE 1 of the invention | Felix (wet- mild palatant added by manufacturer) + 1% Flavour B |

A 1% concentration of Flavour A and Flavour B were used ad compared with 1.25% of Protein Hydrolysate HIE 1 to balance the dry matter content of end recipes. For both test set-ups, 20 qualified cats were fed with recipe 1 (1.1 or 2.1) and recipe 2 (1.2 or 2.2) for a total of four days. Palatability enhancement was measured as a function of percentage diet consumed and percentage of first choice.

Results

The results of this trial are mentioned in table 13.

TABLE 13

Results of cat palatability trial

| Parameter | Recipe 1 | Recipe 2 |
|---|---|---|
| | Test setup 1 | |
| | Felix (wet- mild palatant added) + 1.25% Protix Protein Hydrolysate | Felix (wet- mild palatant added) + 1% Flavour A |
| % Diet consumption | 62% | 38% |
| % First Choice | 57% | 43% |
| | Test setup 2 | |
| | Felix (wet- mild palatant added) + 1.25% Protix Protein Hydrolysate | Felix (wet- mild palatant added) + 1% Flavour B |
| % Diet consumption | 63% | 37% |
| % First Choice | 68% | 32% |

In both the cases the Protein Hydrolysate HIE 1 containing diets were consumed more than the cat food enriched with an equal amount (based on dry matter) of commercially available Flavour A and Flavour B. Additionally, the Protein Hydrolysate HIE 1 containing diets of the invention were also the first choice for the test cats.

Conclusion

The Protein Hydrolysate HIE 1 is an improved cat food palatability enhancer compared with currently available cat food palatability enhancers, when applied at the same dose in cat food.

Example 5

Protein Hydrolysate—Dog Palatability Testing

Objective of Example 5

Showing the potential of HIE 2 as dog food palatability enhancer.

Materials and Methods

Details of feed production are mentioned below:
Dry feed (kibbles) were used for dog palatability testing
Kibbles (containing relatively mild concentrations of palatant) were bought from a local supermarket (The Netherlands). These kibbles were used as control.
Test dog feed preparation was produced by coating 0.5%, 1.25% and 2.5% of concentrated HIE 2 (5 times concentrated using an evaporator) based on the total volume of the diluted HIE 2 solution, wherein HIE 2 is diluted in water, on the kibbles. The test preparation was allowed to dry and temper at room temperature for 1 week after coating.

Details of palatability enhancement testing are:
Control preparation and test preparation were offered to dogs for palatability testing.
Design:
Number of dogs: 20
Duration of testing: 4 days
Portion size: 100 g/dog/day of test preparation and control preparation, each
2 portions (1 test preparation and 1 control preparation) was offered to dogs in the morning. The weight of left-over feed was measured the next morning (exactly after 24 h) and recorded. Portion with less left-over was considered more palatable.

Results and Discussion

The % of feed consumption results and the % of first choice for the dogs results related to diets containing 0.5%, 1.25% and 2.5% concentrated HIE 2, i.e. the test preparations, are displayed in FIG. 9A, FIG. 9B and FIG. 9C, respectively.

For all three tests including test preparations, the % consumption of diets containing HIE 2, a test preparation, was higher than consumption of control diets. Similarly, in all three test cases the % of first choice of diets containing HIE 2 was also higher than the % of first choice of control diets. These results demonstrate the relatively strong palatability enhancement potential of HIE 2 in dog diets when compared to conventional dog feed. Palatability effect is attributed to for example and amongst others the presence of high levels of free amino acids and short chain peptides in HIE 2.

Conclusion

HIE 2 has palatability enhancement potential in dog diets, e.g. relatively strong palatability enhancement potential in dog diets when compared to conventional current dog feed.

Example 6

Assessment of HIE 1 as a Palatability Enhancer in Feed for Whiteleg Shrimp (L. Vannamei)

Introduction

Pontus Research (United Kingdom) demonstrated in this example the strength and potency and suitability of hydrolysed protein HIE 1 of the invention (In Example 6 also referred to as 'HSW') as a palatability enhancer in feeds for white leg shrimp (L. vannamei).

Trial Design and Methods

The demonstration of the strength and potency and suitability of hydrolysed protein HIE 1 as a palatability enhancer in feeds for white leg shrimp (*L. vannamei*) was performed according to the test details outlined in the following Tables A-G.

TABLE A

| Test material | |
|---|---|
| Test material | Protein hydrolysate HIE 1 |
| Mode of action | Insect protein hydrolysate acting as an attractant |
| Example | To demonstrate the palatability of test feed comprising the HIE 1 of the invention trialled in Whiteleg shrimps (*L. vannamei*) against an industry standard feed |

TABLE B

| Test species | |
|---|---|
| Species | *L. vannamei* |
| Source | Global Blue Technologies |

TABLE C

| Test facility | |
|---|---|
| Type | Custom built test chamber for palatability tests, 10 × 140 litre holding tanks. |
| Number and size of tanks | 1 × 140 litre test chamber, 10 × 70 litre holding tanks |
| Incoming water | Carbon filtered mains water. |
| Mechanical and biological filtration | Air driven sponge filter - test chamber; full RAS - holding tanks |
| Disinfection | UV - holding tanks |
| Tank water exchange | 70 l/h - holding tanks |
| System water exchange | 10%/day - holding tanks |
| Target $NH_3$ | <0.03 mg/l. |
| Target $NO_2$ | <0.6 mg/l. |
| Target $NO_3$ | <75 mg/l. |
| Water chemistry testing | 2 times/week using HANNA Multiparameter Bench Photometer. |
| Temperature control | Submersible heaters - test chamber, inline heater - holding tanks. |
| pH control | Automatic. |
| Monitoring | Manual, daily - oxygen, pH, temperature |

TABLE D

| Experimental feeds | |
|---|---|
| Supply | Formulated by Pontus Research, manufactured by Sparos (Portugal). |
| Number of feeds | 4. |
| Description | Two experimental feeds and two standard commercial feed. |
| Expected FCR | ~1.5. |
| Feed required - total no. animals × weight gain × FCR | 2 kg per feed incl. 20% contingency. |

TABLE E

| | Feed design (formulation allowing) | | | |
|---|---|---|---|---|
| | Feed | | | |
| | 0% HSW + squid meal + krill oil | 0% HSW − squid meal − krill oil | 1% HSW − squid meal − krill oil | 2% HSW − squid meal − krill oil |
| Code (label) | 1 | 3 | 2 | 4 |
| Fishmeal LT70 NORVIK | 300.0 | 300.0 | 300.0 | 300.0 |
| Rapeseed meal - 13042018 | 0.0 | 0.0 | 0.0 | 0.0 |
| Soybean meal 48 | 193.0 | 250.0 | 240.3 | 230.7 |
| Soya concentrate | 0.0 | 0.0 | 0.0 | 0.0 |
| Corn gluten | 0.0 | 0.0 | 0.0 | 0.0 |

TABLE E-continued

Feed design (formulation allowing)

| | Feed | | | |
|---|---|---|---|---|
| | 0% HSW + squid meal + krill oil | 0% HSW − squid meal − krill oil | 1% HSW − squid meal − krill oil | 2% HSW − squid meal − krill oil |
| Whole peas | 0.0 | 0.0 | 0.0 | 0.0 |
| Wheat gluten | 0.0 | 0.0 | 0.0 | 0.0 |
| Wheat | 417.8 | 389.6 | 389.6 | 389.8 |
| Squid meal 83 08SP | 30.0 | 0.0 | 0.0 | 0.0 |
| HSW | 0.0 | 0.0 | 10.0 | 20.0 |
| Fish oil - BL75056-V19095-02 | 34.7 | 46.0 | 45.9 | 45.7 |
| Krill oil - 15/130517 | 10.0 | 0.0 | 0.0 | 0.0 |
| Premix | 10.0 | 10.0 | 10.0 | 10.0 |
| Methionine | 0.0 | 0.0 | 0.0 | 0.0 |
| Lysine | 0.0 | 0.0 | 0.0 | 0.0 |
| Antioxidant | 0.0 | 0.0 | 0.0 | 0.0 |
| Vit C | 0.0 | 0.0 | 0.0 | 0.0 |
| Yttrium oxide | 0.0 | 0.0 | 0.0 | 0.0 |
| Guar gum | 0.0 | 0.0 | 0.0 | 0.0 |
| CaCO3 | 3.5 | 3.6 | 3.8 | 3.8 |
| MCP | 1.0 | 0.8 | 0.4 | 0.0 |
| | 1000.0 | 1000.0 | 1000.0 | 1000.0 |

TABLE F

| Trial | |
|---|---|
| Trial design | Single factor replicated study |
| Replicates | 10. |
| Total no. of tanks utilised | 11 - one test chamber and 10 holding tanks. |
| Target start weight g | 30-35 g. |
| Animals per test chamber | 10. |
| Total animals | >220 |
| Feeding regime | Single feeding event per group. |
| Trial period (expected) | Palatability - 10 days - 2 feeding events per day. Time to strike - 4 days - 5 feeding events per feed per size class. |
| Acclimatisation duration | 30 minutes. |
| Light/dark cycle | 12/12. |
| Temperature | 28.0 ± 1° C. |
| pH | 8.00 ± 0.25. |
| Oxygen | >80% saturation. |
| Salinity | 15 ppt. |

TABLE G

| | Data and sample collection and analysis |
|---|---|
| Palatability and time to strike combined | 10 shrimp placed in "acclimatise" chamber as per the image below but modified to include additional feed chamber. 30 minutes to acclimatise. 2 g of a single feed randomly placed in either chamber A, B C or D. 10 minutes while the feed "smell" disperses. Shutter is lifted. Time taken for first shrimp to begin feeding recorded. At 1, 2 5 10 and 15 minutes the number of shrimps in each chamber is recorded. This is repeated 5 times per feed to build a robust data set. Between repeats tank is completely drained and cleaned to ensure no "smell" remains. The above steps are repeated for each size class. Time taken would be approximately 20 hours in total. |

Data Calculations and Statistical Treatments

All data was analysed statistically to determine significance of differences between means using R version 4.0.2 using the following protocol:
  Palatability data was analysed using a Poisson regression model with the addition of a dispersion parameter. Treatments including krill oil were included as a dummy variable and treatments including HSW were treated as a continuous variable.
  Time-to-strike data was analysed using Analysis of Variance command, with a Shapiro-Wilk test for normality and a Levene's test for homogeneity of variance.
  If normality and homogeneity of variance was confirmed, the ANOVA result was accepted.
  If a statistically significant ANOVA result was determined ($p<0.05$) a Tukeys pairwise post hoc analysis was carried out to determine which treatments were different from which other treatments at the $p<0.05$.
  If normality and homogeneity of variance was not confirmed, a Kruskall-Wallace nonparametric test was carried out on the data with a Conover-Iman pairwise post hoc analysis was carried out to determine which treatments were different from which other treatments.
This information is displayed as a one of following denotations:
  ND—no statistical difference, ANOVA or Kruskall-Wallace $p>0.05$
  $p<0.05$—post hoc pairwise analysis showing a significant statistical difference at a confidence level of $p<0.05$
Any data considered outliers were removed from the data.

Results

Palatability

In Table 14, the palatability results are summarized.

TABLE 14

Palatability results. The average shrimp count for each diet over time (±standard error).

| Time (minutes) | 0% HSW − squid meal − krill oil | 0% HSW + squid meal + krill oil | 1% HSW − squid meal − krill oil | 2% HSW − squid meal − krill oil |
|---|---|---|---|---|
| 1 | 0.2 ± 0.18 | 0.00 ± 0.00 | 0.6 ± 0.54 | 0.2 ± 0.18 |
| 2 | 0.4 ± 0.22 | 0.00 ± 0.00 | 0.8 ± 0.52 | 0.4 ± 0.22 |
| 5 | 0.8 ± 0.52 | 0.4 ± 0.22 | 1.6 ± 0.83 | 0.8 ± 0.44 |
| 10 | 1.4 ± 0.61 | 1.8 ± 0.77 | 2.4 ± 1.04 | 3.6 ± 0.73 |
| 15 | 1.2 ± 0.33 | 2.8 ± 0.66 | 2.4 ± 0.92 | 4.6 ± 0.88 |

FIG. 10A displays the predicted performance fit for each diet over time (indicated with an arrow), based on the Jittered count observations at each time interval.

Time to Strike

Table 15 summarizes the time to strike for the shrimps.

TABLE 15

Time to strike. The average length of time (seconds) taken for one shrimp to start feeding. Different superscript letters demonstrate where statistically significant differences were noted between diet groups ($p < 0.05$).

| 0% HSW − squid meal − krill oil | 0% HSW + squid meal + krill oil | 1% HSW − squid meal − krill oil | 2% HSW − squid meal − krill oil |
|---|---|---|---|
| 490.20 ± 171.30[a] | 426.80 ± 99.05[a] | 366.20 ± 139.22[a] | 282.60 ± 77.61[a] |

In FIG. 10B the time to strike is displayed. Average length of time for one shrimp to begin feeding on a diet, showing standard error. Different superscript letters demonstrate where statistically significant differences were noted between diet groups (p<0.05).

No significant differences in shrimp counts were observed between 0% HSW+squid meal+krill oil and 0% HSW— squid meal—krill oil (p>0.05).

1% HSW— squid meal—krill oil had significantly more shrimp counts compared to 0% HSW— squid meal—krill oil (p<0.05).

2% HSW— squid meal—krill oil had significantly more shrimp counts compared to 0% HSW— squid meal—krill oil (p<0.05).

A faster time-to-strike was observed for the 1% HSW— squid meal—krill oil group and the 2% HSW— squid meal—krill oil group, when compared to both the diets 0% HSW+squid meal+krill oil and 0% HSW— squid meal—krill oil (p>0.05) (p>0.05).

DISCUSSION AND CONCLUSIONS

HIE 1 (referred to here as HSW) inclusion at 1% and 2% significantly increased shrimp count when compared to both control diets, the inclusion of krill oil had no significant effect on shrimp count. Time-to-strike decreased in treatments containing HIE 1 and krill oil, and the test feed comprising 2% HSW (=HIE 1) had the largest effect by decreasing time-to-strike by 42.6% compared to the negative control.

REFERENCES

Anuar, M. A. K., Narashid, N. H. H., Salleh, M. M., Yahya, A., 2017. Conversion of chicken viscera into protein hydrolysate for palatant production. *Malaysian Journal of Fundamental and Applied Sciences* 13, 606-611. https://doi.org/10.11113/mjfas.v0n0.615

Clark, J. E., 1998. Taste and flavour: their importance in food choice and acceptance. *Proceedings of the Nutrition Society* 57, 639-643. https://doi.org/10.1079/PNS19980093

Dong, C., He, G., Mai, K., Zhou, H., Xu, W., 2016. Palatability of water-soluble extracts of protein sources and replacement of fishmeal by a selected mixture of protein sources for juvenile turbot (Scophthalmus maximus). *J. Ocean Univ. China* 15, 561-567. https://doi.org/10.1007/s11802-016-2898-8

Everson, I., 2008. *Krill: Biology, Ecology and Fisheries.* John Wiley & Sons.

Hou, Y., Wu, Z., Dai, Z., Wang, G., Wu, G., 2017. Protein hydrolysates in animal nutrition: Industrial production, bioactive peptides, and functional significance. *J Anim Sci Biotechnol* 8. https://doi.org/10.1186/s40104-017-0153-9

Kato, H., Rhue, M. R., Nishimura, T., 1989. Role of Free Amino Acids and Peptides in Food Taste, in: Flavor Chemistry, ACS Symposium Series. American Chemical Society, pp. 158-174. https://doi.org/10.1021/bk-1989-0388.ch013

Paul et al. (2016). Grasshoppers as a food source? Review. *BASE*, 20(S1), 337-352.

PEW Charitable Trusts, 2014. Protecting Antartic Krill (Fact Sheet). PEW Charitable Trusts, USA.

Senevirathne, M., Kim, S.-K., 2012. Chapter 32—Utilization of Seafood Processing By-products: Medicinal Applications, in: Kim, S.-K. (Ed.), Advances in Food and Nutrition Research, Marine Medicinal Foods. *Academic Press*, pp. 495-512. https://doi.org/10.1016/B978-0-12-416003-3.00032-9

Tantikitti, C., 2014. Feed palatability and the alternative protein sources in shrimp feed. *Songklanakarin Journal of Science and Technology* 36, 51-55.

Tchorbanov, B., Marinova, M., Grozeva, L., 2011. Debittering of Protein Hydrolysates by Lactobacillus LBL-4 Aminopeptidase [WWW Document]. Enzyme Research. https://doi.org/10.4061/2011/538676

Wisuthiphaet, N., Klinchan, S., Kongruang, S., 2016. Fish Protein Hydrolysate Production by Acid and Enzymatic Hydrolysis. https://doi.org/10.14416/j.ijast.2016.11.004, KMUTNB *Int. J. Appl. Sci. Technol.*, Vol. 9, No. 4, pp. 261-270.

Sergiy Smetana, Eric Schmitt, Alexander Mathys, 2019. Sustainable use of *Hermetia illucens* insect biomass for feed and food: Attributional and consequential life cycle assessment. Resources, *Conservation & Recycling* 144, pp. 285-296.

3. Firmansyah, M.; Abduh, M. Y. Production of protein hydrolysate containing antioxidant activity from *Hermetia illucens*. Hefiyon 2019, 5, e02005, doi:10.1016/j.heliyon.2019.e02005.

4. Zhu, D.; Huang, X.; Tu, F.; Wang, C.; Yang, F. Preparation, antioxidant activity evaluation, and identification of antioxidant peptide from black soldier fly (*Hermetia illucens* L.) larvae. *J. Food Biochem.* 2020, e13186, doi:10.1111/jfbc.13186.

16. Tsumbu, C. N.; Deby-Dupont, G.; Tits, M.; Angenot, L.; Frederich, M.; Kohnen, S.; Mouithys-Mickalad, A.; Serteyn, D.; Franck, T. Polyphenol content and modulatory activities of some tropical dietary plant extracts on the oxidant activities of neutrophils and myeloperoxidase. *Int J Mol Sci* 2012, 13, 628-650, doi:10.3390/ijms13010628.

17. Paul, A. Field border flowering strips as a source of valuable compounds, Gembloux Agro-Bio Tech University of Liege, Gembloux, Belgique, 2017.

20. Firmansyah, M.; Abduh, M. Y. Production of protein hydrolysate containing antioxidant activity from *Hermetia illucens*. HeVon 2019, 5, e02005, doi:10.1016/j.heliyon.2019.e02005.

23. Zhu, D.; Huang, X.; Tu, F.; Wang, C.; Yang, F. Preparation, antioxidant activity evaluation, and identification of antioxidant peptide from black soldier fly (*Hermetia illucens* L.) larvae. *J. Food Biochem.* 2020, e13186, doi:10.1111/jfbc.13186.

24. Smith, P. K.; Krohn, R. I.; Hermanson, G. T.; Mallia, A. K.; Gartner, F. H.; Provenzano, M. D.; Fujimoto, E. K.; Goeke, N. M.; Olson, B. J.; Klenk, D. C. Measurement of protein using bicinchoninic acid. *Anal. Biochem.* 1985, 150, 76-85, doi:10.1016/0003-2697(85)90442-7.

25. Brand-Williams, W.; Cuvelier, M. E.; Berset, C. Use of a free radical method to evaluate antioxidant activity. *LWT—Food Science and Technology* 1995, 28, 25-30, doi:10.1016/50023-6438(95)80008-5.

26. Arnao, M. B.; Cano, A.; Acosta, M. The hydrophilic and lipophilic contribution to total antioxidant activity. *Food Chemistry*), 2001, 73, 239-244, doi:10.1016/S0308-8146(00)00324-1.

27. Franck, T.; Kohnen, S.; Boudjeltia, K. Z.; Van Antwerpen, P.; Bosseloir, A.; Niesten, A.; Gach, O.; Nys, M.; Deby-Dupont, G.; Serteyn, D. A new easy method for specific measurement of active myeloperoxidase in human biological fluids and tissue extracts. *Talanta* 2009, 80, 723-729, doi:10.1016/j.talanta.2009.07.052.

28. Zhang, H.; Holden-Wiltse, J.; Wang, J.; Liang, H. A Strategy to Model Nonmonotonic Dose-Response Curve and Estimate IC50. *PLOS ONE* 2013, 8, e69301, doi: 10.1371/journal.pone.0069301.
29. R Core Team R: *A language and environment for statistical computing*; R Foundation for Statistical Computing: Vienna, Austria, 2017.

The invention claimed is:

1. A method for producing Maillard reaction products of an enzymatically hydrolysed water-soluble insect protein, the method comprising the steps of:
   a) providing an aqueous water-soluble insect protein composition comprising at least one water-soluble protein, preferably more than one water-soluble protein, wherein the pH of said composition is between pH 4 and pH 8 and wherein the at least one water-soluble protein in said water-soluble protein composition is solubilized, and further providing at least one peptidase;
   b) mixing the at least one peptidase of step a) with the aqueous water-soluble insect protein composition of step a), therewith providing a protein/peptidase mixture;
   c) heating the protein/peptidase mixture of step b) at a temperature of below 75° C. such that the at least one water-soluble protein in the protein/peptidase mixture is enzymatically hydrolysed by the at least one peptidase, therewith providing enzymatically hydrolysed protein/peptidase solution; and
   d) terminating the enzymatic hydrolysis in the hydrolysed protein/peptidase solution of step c) by heating the hydrolysed protein/peptidase solution at a temperature of between 75° C. and 110° C., such that the at least one peptidase is heat-inactivated by the heating, therewith providing the enzymatically hydrolysed water-soluble insect protein;
wherein after step d) in a further step e) the enzymatically hydrolysed water-soluble insect protein of step d) is subjected to a Maillard reaction for the provision of modified amino groups in said enzymatically hydrolysed protein, the Maillard reaction comprising the sub-steps:
e1) providing a carbohydrate and mixing the carbohydrate with the enzymatically hydrolysed water-soluble insect protein of step d), therewith providing an enzymatically hydrolysed insect protein/added carbohydrate mixture;
e2) heating the enzymatically hydrolysed insect protein/added carbohydrate mixture of step e1), therewith providing Maillard reaction products of enzymatically hydrolysed insect protein.

2. The method according to claim 1, wherein in step c) the heating is at a temperature of between 35° C. and 60° C., and/or wherein the heating is for a duration of between 2 hours and 12 hours.

3. The method according to claim 1, wherein in step a) the pH of the aqueous water-soluble insect protein composition is between 5 and 7.7; and/or wherein the at least one peptidase provided in step a) is or comprises an aminopeptidase.

4. The method according to claim 1, wherein in step b) the amount of the at least one peptidase in the protein/peptidase mixture is between 0.05% and 7% by weight of the total weight of the protein/peptidase mixture.

5. The method according to claim 1, wherein in step d) the enzymatic hydrolysis in the hydrolysed protein/peptidase solution of step c) is terminated by heating the hydrolysed protein/peptidase solution for a duration of between 30 seconds and 30 minutes; and/or wherein in step d) the enzymatic hydrolysis in the hydrolysed protein/peptidase solution of step c) is terminated by heating the hydrolysed protein/peptidase solution to a temperature of 80° C.-105° C.

6. The method according to claim 1, wherein in step e1) the final concentration of added carbohydrate is between 0.05% and 6.0% by weight of the total weight of the enzymatically hydrolysed insect protein/added carbohydrate mixture; and/or wherein in step e1) the provided carbohydrate is sucrose or glucose or a mixture thereof.

7. The method according to claim 1, wherein in step e2) the enzymatically hydrolysed insect protein/added carbohydrate mixture of step e1) is heated at a temperature of between 100° C. and 170° C.; and/or wherein in step e2) the enzymatically hydrolysed insect protein/added carbohydrate mixture of step e1) is heated for a time period of between 1 minute and 120 minutes.

8. The method according to claim 1, wherein after step e2) in a further step f2) the Maillard reaction products of enzymatically hydrolysed water-soluble insect protein of step e2) are dried, and/or wherein after step e2) in a further step f4) the Maillard reaction products of enzymatically hydrolysed water-soluble insect protein of step e2) are concentrated.

9. The method according to claim 1, wherein the amount of water-soluble insect protein in the protein/peptidase mixture of step b) is between 0.2% and 30% by weight based on the total weight of the protein/enzyme mixture.

10. The method according to claim 1, wherein in step a) the aqueous water-soluble insect protein composition is an aqueous water-soluble insect protein composition derived from any one or more of larvae of beetles, house fly, black soldier fly, locust, grasshopper, cricket, cockroach larvae, palm weevil larvae, silk worm, giant water bug, cicada, bamboo worm, an ant, bush cricket, butterfly, leafhopper, planthopper and bee larvae, and the aqueous water-soluble insect protein composition is preferably derived from larvae of black soldier fly.

11. The method according to claim 1, wherein in step a) the aqueous water-soluble insect protein composition is a water-soluble insect protein composition dissolved in aqueous solution such as water, wherein the aqueous water-soluble insect protein composition is provided by converting insects into at least an aqueous water-soluble insect protein composition by the steps of, or by at least the steps of:
   (i) providing insects, preferably black soldier fly larvae,
   (ii) reducing the insects of step (i) in size, preferably by mincing, then
   (iii) obtaining a pulp from the insects with reduced size of step (ii), then
   (iv) heating the pulp of step (iii) to a temperature of 70-100° C., then
   (v) subjecting the heated pulp of step (iv) to a physical separation step, preferably encompassing decanting and/or centrifugation, thereby providing the insect protein composition, and then
   (vi) mixing the insect protein composition of step (v) in an aqueous solution such as water or an aqueous buffer, preferably water, therewith providing the aqueous water-soluble insect protein composition of step a).

12. The method according to claim 1, wherein the Maillard reaction products of enzymatically hydrolysed water-soluble insect protein provided in step e2) is soluble in an aqueous solution such as water or a buffered aqueous solution to an extent of at least 60% by weight based on the weight of the total amount of the Maillard reaction products of enzymatically hydrolysed water-soluble insect protein provided in step e2).

\* \* \* \* \*